(12) United States Patent
Chow et al.

(10) Patent No.: US 9,149,602 B2
(45) Date of Patent: Oct. 6, 2015

(54) DUAL NEEDLE DELIVERY SYSTEM

(75) Inventors: Mina Chow, Campbell, CA (US);
Dwight A. Ambat, Fremont, CA (US);
Jin Cheng, Livermore, CA (US);
Eugene Michal, San Francisco, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 2115 days.

(21) Appl. No.: 11/112,546

(22) Filed: Apr. 22, 2005

(65) Prior Publication Data
US 2006/0253088 A1    Nov. 9, 2006

(51) Int. Cl.
*A61M 25/00*    (2006.01)
*A61M 25/06*    (2006.01)

(52) U.S. Cl.
CPC ............. *A61M 25/003* (2013.01); *A61M 25/06* (2013.01); *A61M 2025/0034* (2013.01); *A61M 2025/0037* (2013.01)

(58) Field of Classification Search
CPC ............. A61M 2025/0037; A61M 2025/0034; A61M 25/0084; A61M 25/0069; A61M 2025/0096; A61M 2025/0004; A61M 2025/0006; A61M 2025/0008; A61M 25/0026; A61M 25/0028; A61M 2025/0175
USPC ........ 604/284, 164.01, 524, 528, 523, 164.09
See application file for complete search history.

(56) References Cited

U.S. PATENT DOCUMENTS

| | | | |
|---|---|---|---|
| 3,177,543 A | 11/1962 | Fountain | |
| 3,716,058 A | 2/1973 | Tanner et al. | |
| 3,804,097 A * | 4/1974 | Rudie | ............................. 604/28 |
| 4,072,146 A | 2/1978 | Howes | |
| 4,128,100 A | 12/1978 | Wendorff | |
| 4,675,004 A | 6/1987 | Hadford et al. | |
| 4,719,924 A | 1/1988 | Crittenden et al. | |
| 4,781,186 A | 11/1988 | Simpson et al. | |
| 4,808,156 A | 2/1989 | Dean | |
| 4,817,250 A | 4/1989 | Kurosaki | |

(Continued)

FOREIGN PATENT DOCUMENTS

| | | |
|---|---|---|
| DE | 10161543 | 6/2003 |
| EP | 0377269 | 7/1990 |

(Continued)

OTHER PUBLICATIONS

International Search Report and Written Opinion for PCT International Appln. No. US/2006/013909, mailed on Aug. 11, 2006 (13 pages).

(Continued)

*Primary Examiner* — Quynh-Nhu H Vu
*Assistant Examiner* — Bradley Osinski
(74) *Attorney, Agent, or Firm* — Randy Shen; Blakely Sokoloff Taylor & Zafman LLP

(57) ABSTRACT

An apparatus for delivering devices. The apparatus comprises a catheter with an elongated shaft having a first lumen and a second lumen extending therethrough. The apparatus further comprises a distal section with a lumen in communication with a port in a distal end of the catheter and with the first lumen and the second lumen. The first lumen is configured for a first device and the second lumen is configured for a second device to be disposed therein. The apparatus further comprises a proximal adapter coupled to the elongated shaft with a first port in communication with the first lumen and a second port in communication with the second lumen.

15 Claims, 10 Drawing Sheets

(56) References Cited

U.S. PATENT DOCUMENTS

| | | |
|---|---|---|
| 4,830,023 A | 5/1989 | de Toledo et al. |
| 4,920,980 A | 5/1990 | Jackowski |
| 4,927,421 A | 5/1990 | Goble et al. |
| 4,932,962 A | 6/1990 | Yoon et al. |
| 4,994,067 A | 2/1991 | Summers |
| 5,040,548 A | 8/1991 | Yock |
| 5,061,273 A | 10/1991 | Yock |
| 5,100,418 A | 3/1992 | Yoon et al. |
| 5,100,421 A | 3/1992 | Christoudias |
| 5,102,421 A | 4/1992 | Anspach, Jr. |
| 5,116,337 A | 5/1992 | Johnson |
| 5,129,902 A | 7/1992 | Goble et al. |
| 5,141,520 A | 8/1992 | Goble et al. |
| 5,156,616 A | 10/1992 | Meadows et al. |
| 5,163,903 A | 11/1992 | Crittenden et al. |
| 5,171,233 A | 12/1992 | Amplatz et al. |
| 5,201,598 A | 4/1993 | Tehan |
| 5,234,443 A | 8/1993 | Phan et al. |
| 5,242,456 A | 9/1993 | Nash et al. |
| 5,246,441 A | 9/1993 | Ross et al. |
| 5,261,889 A * | 11/1993 | Laine et al. ............... 604/164.11 |
| 5,273,533 A * | 12/1993 | Bonaldo ........................ 604/83 |
| 5,290,244 A * | 3/1994 | Moonka .................. 604/164.13 |
| 5,350,395 A | 9/1994 | Yock |
| 5,352,215 A * | 10/1994 | Thome et al. .................. 604/284 |
| 5,358,479 A | 10/1994 | Wilson |
| 5,370,662 A | 12/1994 | Stone et al. |
| 5,374,275 A | 12/1994 | Bradley et al. |
| 5,383,260 A | 1/1995 | Deschenes et al. |
| 5,431,673 A | 7/1995 | Summers et al. |
| 5,441,483 A | 8/1995 | Avitall |
| 5,451,233 A | 9/1995 | Yock |
| 5,456,667 A | 10/1995 | Ham et al. |
| 5,487,757 A | 1/1996 | Truckai et al. |
| 5,495,974 A | 3/1996 | Deschenes et al. |
| 5,518,162 A | 5/1996 | Deschenes et al. |
| 5,520,700 A | 5/1996 | Beyar et al. |
| 5,522,873 A | 6/1996 | Jackman et al. |
| 5,531,686 A | 7/1996 | Lundquist et al. |
| 5,549,582 A * | 8/1996 | Larsson et al. ................. 604/533 |
| 5,554,184 A | 9/1996 | Machiraju |
| 5,569,277 A | 10/1996 | Evans et al. |
| 5,571,215 A | 11/1996 | Sterman et al. |
| 5,588,188 A | 12/1996 | Jermyn, Jr. |
| 5,609,598 A | 3/1997 | Laufer et al. |
| 5,613,937 A | 3/1997 | Garrison et al. |
| 5,613,954 A * | 3/1997 | Nelson et al. ............ 604/167.03 |
| 5,617,854 A | 4/1997 | Munsif |
| 5,626,613 A | 5/1997 | Schmieding |
| 5,632,754 A | 5/1997 | Farley et al. |
| 5,640,955 A | 6/1997 | Ockuly et al. |
| 5,642,736 A | 7/1997 | Avitall |
| 5,643,319 A | 7/1997 | Green et al. |
| 5,681,280 A | 10/1997 | Rusk et al. |
| 5,681,346 A | 10/1997 | Orth et al. |
| 5,682,906 A | 11/1997 | Sterman et al. |
| 5,687,723 A | 11/1997 | Avitall |
| 5,709,224 A | 1/1998 | Behl et al. |
| 5,728,129 A | 3/1998 | Summers |
| 5,782,828 A | 7/1998 | Chen et al. |
| 5,810,869 A | 9/1998 | Kaplan et al. |
| 5,810,882 A | 9/1998 | Bolduc et al. |
| 5,823,955 A | 10/1998 | Kuck et al. |
| 5,824,008 A | 10/1998 | Bolduc et al. |
| 5,865,800 A | 2/1999 | Mirarchi et al. |
| 5,868,733 A | 2/1999 | Ockuly et al. |
| 5,868,767 A | 2/1999 | Farley et al. |
| 5,916,213 A | 6/1999 | Haissaguerre et al. |
| 5,954,731 A | 9/1999 | Yoon |
| 5,961,440 A | 10/1999 | Schweich, Jr. et al. |
| 5,964,772 A | 10/1999 | Bolduc et al. |
| 5,972,022 A | 10/1999 | Huxel |
| 5,989,284 A | 11/1999 | Laufer |
| 6,001,095 A | 12/1999 | de la Rama et al. |
| 6,001,104 A | 12/1999 | Benderev et al. |
| 6,001,127 A | 12/1999 | Schoon et al. |
| 6,004,332 A | 12/1999 | Yoon et al. |
| 6,017,358 A | 1/2000 | Yoon et al. |
| 6,021,340 A | 2/2000 | Randolph et al. |
| 6,027,514 A | 2/2000 | Stine |
| 6,036,715 A | 3/2000 | Yock |
| 6,045,497 A | 4/2000 | Schweich, Jr. et al. |
| 6,050,936 A | 4/2000 | Schweich, Jr. et al. |
| 6,051,008 A | 4/2000 | Saadat et al. |
| 6,059,715 A | 5/2000 | Schweich, Jr. et al. |
| 6,066,100 A * | 5/2000 | Willard et al. ................. 600/452 |
| 6,077,214 A | 6/2000 | Mortier et al. |
| 6,090,096 A | 7/2000 | St. Goar et al. |
| 6,093,199 A | 7/2000 | Brown et al. |
| 6,110,100 A | 8/2000 | Talpade |
| 6,113,609 A | 9/2000 | Adams |
| 6,117,176 A | 9/2000 | Chen |
| 6,120,520 A | 9/2000 | Saadat et al. |
| 6,123,699 A | 9/2000 | Webster, Jr. |
| 6,149,669 A | 11/2000 | Li |
| 6,152,943 A * | 11/2000 | Sawhney ........................ 606/193 |
| 6,161,543 A | 12/2000 | Cox et al. |
| 6,162,168 A | 12/2000 | Schweich, Jr. et al. |
| 6,164,283 A | 12/2000 | Lesh |
| 6,165,119 A | 12/2000 | Schweich, Jr. et al. |
| 6,165,120 A | 12/2000 | Schweich, Jr. et al. |
| 6,165,164 A | 12/2000 | Hill et al. |
| 6,165,183 A | 12/2000 | Kuehn et al. |
| 6,165,197 A | 12/2000 | Yock |
| 6,174,323 B1 | 1/2001 | Biggs et al. |
| 6,176,240 B1 | 1/2001 | Nikolchev et al. |
| 6,178,346 B1 | 1/2001 | Amundson et al. |
| 6,179,840 B1 | 1/2001 | Bowman |
| 6,182,664 B1 | 2/2001 | Cosgrove |
| 6,183,411 B1 | 2/2001 | Mortier et al. |
| 6,187,040 B1 | 2/2001 | Wright |
| 6,190,401 B1 | 2/2001 | Green et al. |
| 6,190,408 B1 | 2/2001 | Melvin |
| 6,200,302 B1 | 3/2001 | Johnson |
| 6,203,531 B1 | 3/2001 | Ockuly et al. |
| 6,210,378 B1 | 4/2001 | Ouchi |
| 6,210,407 B1 | 4/2001 | Webster, Jr. |
| 6,210,432 B1 | 4/2001 | Solem et al. |
| 6,231,561 B1 | 5/2001 | Frazier et al. |
| 6,231,587 B1 | 5/2001 | Makower |
| 6,241,728 B1 | 6/2001 | Gaiser et al. |
| 6,254,568 B1 | 7/2001 | Ponzi |
| 6,254,598 B1 | 7/2001 | Edwards et al. |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,267,781 B1 | 7/2001 | Tu |
| 6,269,819 B1 | 8/2001 | Oz et al. |
| 6,270,526 B1 | 8/2001 | Cox |
| 6,283,127 B1 | 9/2001 | Sterman et al. |
| 6,283,962 B1 | 9/2001 | Tu et al. |
| 6,290,674 B1 | 9/2001 | Roue et al. |
| 6,299,622 B1 | 10/2001 | Snow et al. |
| 6,306,133 B1 | 10/2001 | Tu et al. |
| 6,312,447 B1 | 11/2001 | Grimes |
| 6,325,823 B1 | 12/2001 | Horzewski et al. |
| 6,355,030 B1 | 3/2002 | Adrich et al. |
| 6,371,978 B1 | 4/2002 | Wilson |
| 6,374,476 B1 | 4/2002 | Ponzi et al. |
| 6,379,373 B1 | 4/2002 | Sawhney et al. |
| 6,402,780 B2 | 6/2002 | Williamson, IV et al. |
| 6,402,781 B1 | 6/2002 | Langberg et al. |
| 6,408,214 B1 | 6/2002 | Williams et al. |
| 6,419,696 B1 | 7/2002 | Ortiz et al. |
| 6,436,110 B2 | 8/2002 | Bowman et al. |
| 6,447,517 B1 | 9/2002 | Bowman |
| 6,461,366 B1 | 10/2002 | Seguin |
| 6,482,224 B1 | 11/2002 | Michler et al. |
| 6,488,689 B1 | 12/2002 | Kaplan et al. |
| 6,493,575 B1 | 12/2002 | Kesten et al. |
| 6,497,707 B1 | 12/2002 | Bowman et al. |
| 6,500,167 B1 | 12/2002 | Webster, Jr. |
| 6,517,553 B2 | 2/2003 | Klein et al. |
| 6,537,198 B1 | 3/2003 | Vidlund et al. |

(56) References Cited

U.S. PATENT DOCUMENTS

| | | | |
|---|---|---|---|
| 6,537,314 B2 | 3/2003 | Langberg et al. |
| 6,551,271 B2 | 4/2003 | Nguyen |
| 6,554,794 B1 | 4/2003 | Mueller et al. |
| 6,554,852 B1 | 4/2003 | Oberlander |
| 6,575,998 B2 | 6/2003 | Beyar |
| 6,585,718 B2 | 7/2003 | Hayzelden et al. |
| 6,599,311 B1 | 7/2003 | Biggs et al. |
| 6,605,086 B2 | 8/2003 | Hayzelden et al. |
| 6,610,033 B1 | 8/2003 | Melanson et al. |
| 6,610,058 B2 | 8/2003 | Flores |
| 6,619,291 B2 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,638,286 B1 | 10/2003 | Burbank et al. |
| 6,648,903 B1 | 11/2003 | Pierson, III |
| 6,656,221 B2 | 12/2003 | Taylor et al. |
| 6,676,702 B2 | 1/2004 | Mathis |
| 6,706,011 B1 | 3/2004 | Murphy-Chutorian et al. |
| 6,706,065 B2 | 3/2004 | Langberg et al. |
| 6,709,442 B2 | 3/2004 | Miller et al. |
| 6,709,456 B2 | 3/2004 | Langberg et al. |
| 6,712,804 B2 | 3/2004 | Roue et al. |
| 6,718,985 B2 | 4/2004 | Hlavka et al. |
| 6,719,767 B1 | 4/2004 | Kimblad |
| 6,723,038 B1 | 4/2004 | Schroeder |
| 6,733,500 B2 | 5/2004 | Kelley et al. |
| 6,746,472 B2 | 6/2004 | Frazier et al. |
| 6,755,812 B2 | 6/2004 | Peterson et al. |
| 6,761,734 B2 | 7/2004 | Suhr |
| 6,764,510 B2 | 7/2004 | Vidlund et al. |
| 6,770,066 B1 | 8/2004 | Weaver et al. |
| 6,770,070 B1 | 8/2004 | Balbierz |
| 6,780,167 B2 | 8/2004 | Leone |
| 6,790,231 B2 | 9/2004 | Liddicoat et al. |
| 6,800,090 B2 | 10/2004 | Alferness et al. |
| 6,808,510 B1 | 10/2004 | DiFiore |
| 6,810,882 B2 | 11/2004 | Langberg et al. |
| 6,824,562 B2 | 11/2004 | Mathis et al. |
| 6,852,124 B2 | 2/2005 | Cox et al. |
| 6,890,353 B2 | 5/2005 | Cohn et al. |
| 6,905,476 B2 | 6/2005 | Ponzi |
| 6,908,478 B2 | 6/2005 | Alferness et al. |
| 6,911,035 B1 | 6/2005 | Blomme |
| 6,921,391 B1* | 7/2005 | Barker et al. | 604/284 |
| 6,951,549 B1 | 10/2005 | Beyerlein |
| 6,960,229 B2 | 11/2005 | Mathis et al. |
| 6,964,683 B2 | 11/2005 | Kowalsky et al. |
| 6,966,926 B2 | 11/2005 | Mathis |
| 6,989,028 B2 | 1/2006 | Lashinki et al. |
| 6,997,951 B2 | 2/2006 | Solem et al. |
| 7,073,504 B2 | 7/2006 | Callister et al. |
| 7,087,064 B1 | 8/2006 | Hyde |
| 7,104,999 B2 | 9/2006 | Overaker |
| 7,160,318 B2 | 1/2007 | Greenberg et al. |
| 7,186,264 B2 | 3/2007 | Liddicoat et al. |
| 7,247,149 B2 | 7/2007 | Beyerlein |
| 7,364,567 B2 | 4/2008 | Beyerlein |
| 2001/0003986 A1 | 6/2001 | Cosgrove |
| 2001/0005787 A1 | 6/2001 | Oz et al. |
| 2001/0018611 A1 | 8/2001 | Solem et al. |
| 2001/0027322 A1 | 10/2001 | Bowman |
| 2001/0044568 A1 | 11/2001 | Langberg et al. |
| 2002/0010483 A1 | 1/2002 | Folmer et al. |
| 2002/0010486 A1 | 1/2002 | Hirt |
| 2002/0013571 A1 | 1/2002 | Goldfarb et al. |
| 2002/0016628 A1 | 2/2002 | Langberg et al. |
| 2002/0026216 A1 | 2/2002 | Grimes |
| 2002/0035361 A1 | 3/2002 | Houser et al. |
| 2002/0042651 A1 | 4/2002 | Liddicoat et al. |
| 2002/0049414 A1* | 4/2002 | Nobles et al. | 604/187 |
| 2002/0077647 A1 | 6/2002 | Snow et al. |
| 2002/0087169 A1 | 7/2002 | Brock et al. |
| 2002/0087173 A1 | 7/2002 | Alferness et al. |
| 2002/0103492 A1 | 8/2002 | Kaplan et al. |
| 2002/0103532 A1 | 8/2002 | Langberg et al. |
| 2002/0103533 A1 | 8/2002 | Langberg et al. |
| 2002/0111637 A1 | 8/2002 | Kaplan et al. |
| 2002/0161330 A1 | 10/2002 | Nguyen |
| 2002/0165484 A1 | 11/2002 | Bowe et al. |
| 2002/0165533 A1 | 11/2002 | Flores |
| 2002/0165534 A1 | 11/2002 | Hayzelden et al. |
| 2002/0169502 A1 | 11/2002 | Mathis |
| 2002/0169504 A1 | 11/2002 | Alferness |
| 2002/0183835 A1 | 12/2002 | Taylor et al. |
| 2002/0183836 A1 | 12/2002 | Liddicoat et al. |
| 2002/0183837 A1 | 12/2002 | Streeter et al. |
| 2002/0183841 A1 | 12/2002 | Cohn et al. |
| 2002/0188170 A1 | 12/2002 | Santamore et al. |
| 2003/0050598 A1 | 3/2003 | Hayzelden et al. |
| 2003/0069593 A1 | 4/2003 | Tremulis et al. |
| 2003/0078465 A1 | 4/2003 | Pai et al. |
| 2003/0083538 A1 | 5/2003 | Adams et al. |
| 2003/0093071 A1 | 5/2003 | Hauck et al. |
| 2003/0105520 A1 | 6/2003 | Alferness et al. |
| 2003/0120340 A1 | 6/2003 | Liska et al. |
| 2003/0120341 A1 | 6/2003 | Shennib et al. |
| 2003/0130731 A1 | 7/2003 | Vidlund et al. |
| 2003/0135199 A1* | 7/2003 | Rosenman et al. | 604/528 |
| 2003/0144697 A1 | 7/2003 | Mathis |
| 2003/0144732 A1 | 7/2003 | Cosgrove et al. |
| 2003/0167071 A1 | 9/2003 | Martin et al. |
| 2003/0171776 A1 | 9/2003 | Adams et al. |
| 2003/0212453 A1 | 11/2003 | Mathis et al. |
| 2003/0216764 A1 | 11/2003 | Tu et al. |
| 2004/0002692 A1 | 1/2004 | Claude et al. |
| 2004/0010231 A1 | 1/2004 | Leonhardt et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0059314 A1 | 3/2004 | Schon et al. |
| 2004/0059351 A1 | 3/2004 | Eigler et al. |
| 2004/0064098 A1 | 4/2004 | Cuschieri et al. |
| 2004/0098092 A1 | 5/2004 | Butaric et al. |
| 2004/0122418 A1 | 6/2004 | Voorhees |
| 2004/0138683 A1 | 7/2004 | Shelton et al. |
| 2004/0138744 A1 | 7/2004 | Lashinski et al. |
| 2004/0148020 A1 | 7/2004 | Vidlund et al. |
| 2004/0153147 A1 | 8/2004 | Mathis |
| 2004/0167463 A1 | 8/2004 | Zawacki et al. |
| 2004/0204683 A1* | 10/2004 | McGuckin et al. | 604/173 |
| 2005/0045183 A1 | 3/2005 | Callister et al. |
| 2005/0055089 A1 | 3/2005 | Macoviak et al. |
| 2005/0080476 A1* | 4/2005 | Gunderson et al. | 623/1.11 |
| 2005/0085844 A1 | 4/2005 | Tremulis et al. |
| 2005/0096629 A1* | 5/2005 | Gerber et al. | 604/506 |
| 2005/0187519 A1* | 8/2005 | Harris et al. | 604/117 |
| 2005/0197635 A1* | 9/2005 | Greydanus et al. | 604/284 |
| 2005/0209633 A1 | 9/2005 | Callister et al. |
| 2005/0267571 A1 | 12/2005 | Spence et al. |
| 2005/0267573 A9 | 12/2005 | Macoviak et al. |
| 2006/0041306 A1 | 2/2006 | Vidlund et al. |
| 2006/0095025 A1 | 5/2006 | Levine et al. |
| 2006/0282161 A1 | 12/2006 | Huynh et al. |
| 2007/0078437 A1* | 4/2007 | Borden et al. | 604/523 |
| 2008/0021417 A1* | 1/2008 | Zawacki et al. | 604/284 |

FOREIGN PATENT DOCUMENTS

| | | |
|---|---|---|
| EP | 0570102 A1 | 11/1993 |
| WO | WO-9900059 | 1/1999 |
| WO | WO-9913777 | 3/1999 |
| WO | WO-9930647 | 6/1999 |
| WO | WO-9944534 | 9/1999 |
| WO | WO-0003759 | 1/2000 |
| WO | WO-0006026 | 2/2000 |
| WO | WO-0006027 | 2/2000 |
| WO | WO-0006028 | 2/2000 |
| WO | WO-0016700 | 3/2000 |
| WO | WO-0060995 | 10/2000 |
| WO | WO-0100111 | 1/2001 |
| WO | WO-0100114 | 1/2001 |
| WO | WO-0126557 | 4/2001 |
| WO | WO-0128432 | 4/2001 |

(56) References Cited

FOREIGN PATENT DOCUMENTS

| WO | WO-0128455 | 4/2001 |
|---|---|---|
| WO | WO-0149213 | 7/2001 |
| WO | WO-0154618 | 8/2001 |
| WO | WO-0189440 | 11/2001 |
| WO | WO-0200099 | 1/2002 |
| WO | WO-0201999 | 1/2002 |
| WO | WO-0234167 | 5/2002 |
| WO | WO-0239925 | 5/2002 |
| WO | WO-02053206 | 7/2002 |
| WO | WO-02060352 | 8/2002 |
| WO | WO-02062263 | 8/2002 |
| WO | WO-02062270 | 8/2002 |
| WO | WO-02062408 | 8/2002 |
| WO | WO-02063533 | 8/2002 |
| WO | WO-02078576 | 10/2002 |
| WO | WO-03049619 | 6/2003 |
| WO | WO-03073913 | 9/2003 |
| WO | WO-2004012789 | 2/2004 |
| WO | WO-2004014282 | 2/2004 |
| WO | WO-2004045463 | 6/2004 |

OTHER PUBLICATIONS

Abbott Cardiovascular Systems, Non final office action dated Aug. 19, 2008 for U.S. Appl. No. 10/740,360, (Aug. 19, 2008), 8 pages.
Abbott Cardiovascular Systems, PCT International Preliminary Report on Patentability and Written Opinion for PCT Appln No. US2004/031403, mailed Apr. 13, 2006.
Abbott Cardiovascular Systems, PCT International Search Report and Written Opinion of the International Searching Authority for PCT Appln No. US2004/031403, mailed May 18, 2005.
Abbott Cardiovascular Systems, PCT International Search Report for PCT Appln No. US2004/031403, mailed Feb. 15, 2005.
Abbott Cardiovascular Systems, Final Office Action dated Apr. 15, 2009 for U.S. Appl. No. 10/676,616.
Abbott Cardiovascular Systems, Non final office action dated Jun. 12, 2009 for U.S. Appl. No. 11/240,589.
Abbott Cardiovascular Systems, Final Office Action dated Aug. 3, 2009 for U.S. Appl. No. 10/464,132.
Abbott Cardiovascular Systems, Final Office Action dated Mar. 24, 2009 for U.S. Appl. No. 10/740,360.
Abbott Cardiovascular Systems, Final office action dated Dec. 28, 2009 for U.S. Appl. No. 11/240,589.
Abbott Cardiovascular Systems, Non final office action dated Feb. 23, 2010 for U.S. Appl. No. 10/464,132.
Abbott Cardiovascular Systems, Final office action dated Aug. 3, 2010 for U.S. Appl. No. 10/464,132.
Abbott Cardiovascular Systems, Final Office Action mailed Dec. 14, 2010 for U.S. Appl. No. 11/445,694, 12 pages.
Abbott Cardiovascular Systems, First notice of reasons for refusal dated Apr. 26, 2011 for JP Appln. No. 2008-507728.
Abbott Cardiovascular Systems, PCT Invitation to Pay Additional Fees for PCT International Appln. No. PCT/US03/36633, mailed May 19, 2004.
Bonow, Robert O., et al., "Guidelines for the Management of Patients with Valvular Health Disease", Report of American College of Cardiology/American Heart Assoc. Task Force on Practice Guidelines, (Committee on Management of Patients with Valvular Heart Disease), American College of Cardiology and American Heart Assoc., Inc., (1998), pp. 1949-1984.
Messas, et al., "Chordal Cutting a New Therapeutic approach for Ischmic Mitral Regurgitation", American heart Association Inc., (2001), 1958-1963.
Abbott Cardiovascular Systems, PCT Search Report and Written Opinion dated Nov. 16, 2007 for PCT/US2007/011948.
Abbott Cardiovascular Systems, Non-Final Office Action mailed May 20, 2010 for U.S. Appl. No. 11/445,694.
Abbott Cardiovascular Systems, Examination report mailed Apr. 7, 2015 for EP06750070.2.

* cited by examiner

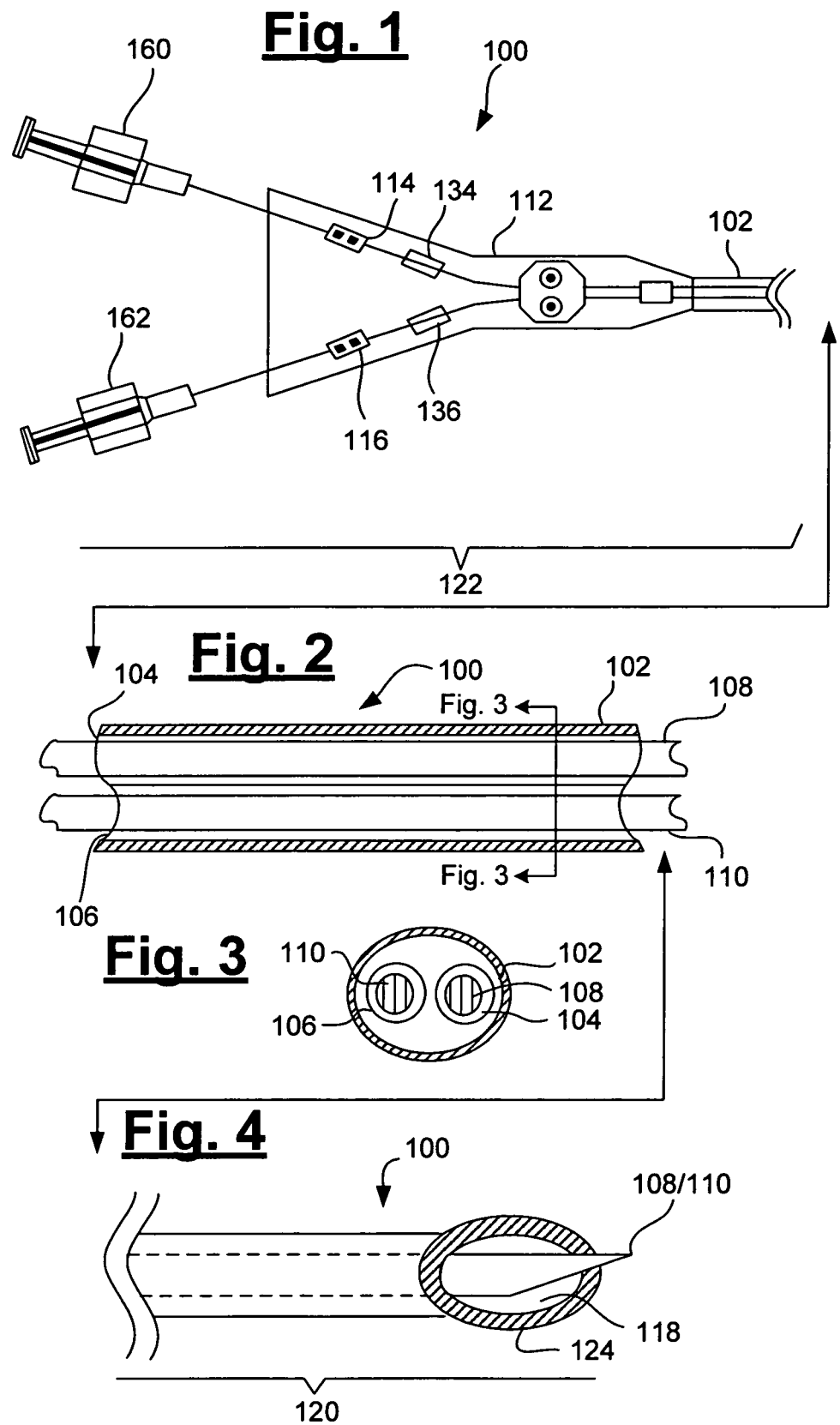

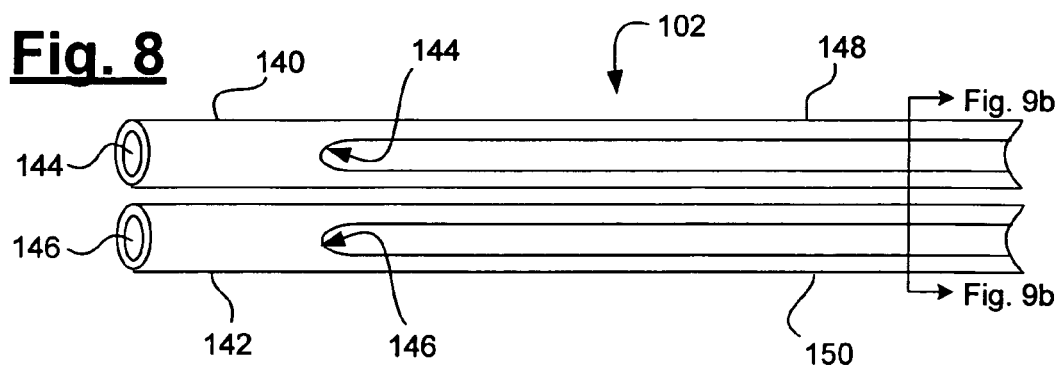
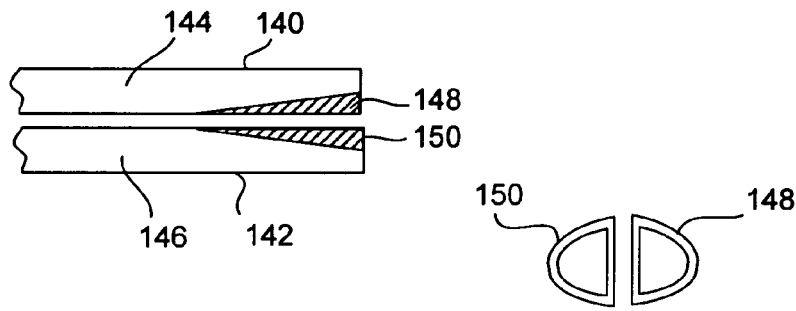
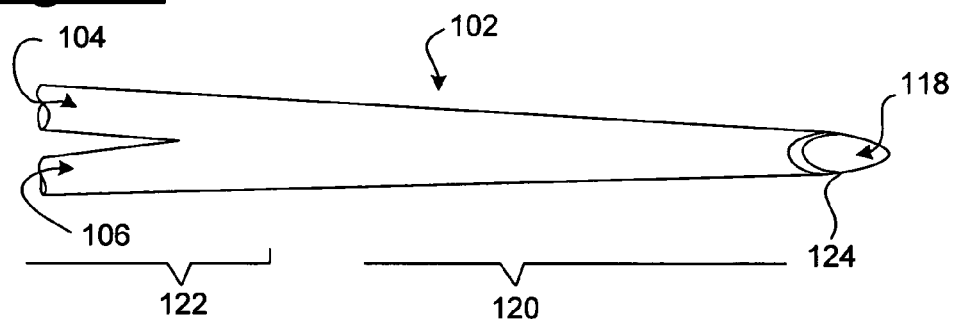
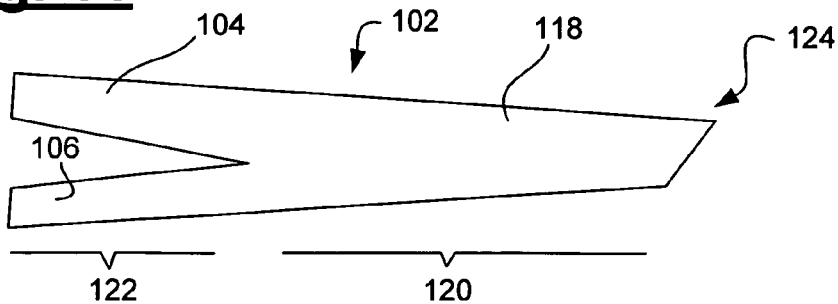

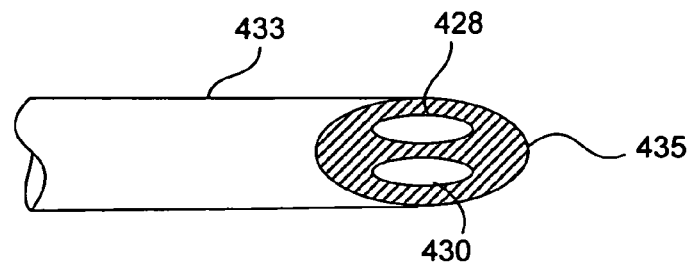
Fig. 23
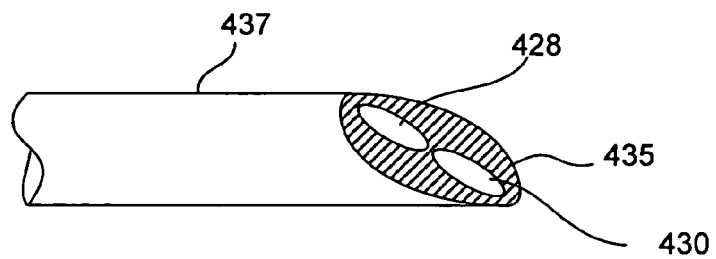
Fig. 24
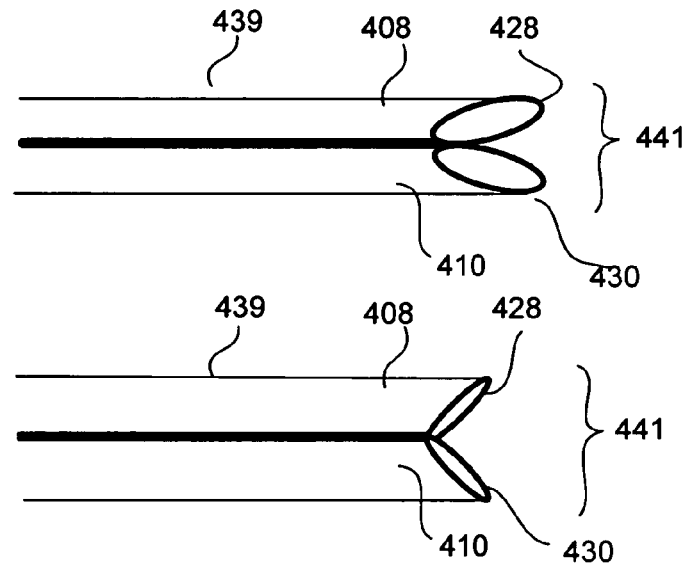
Fig. 25
Fig. 26
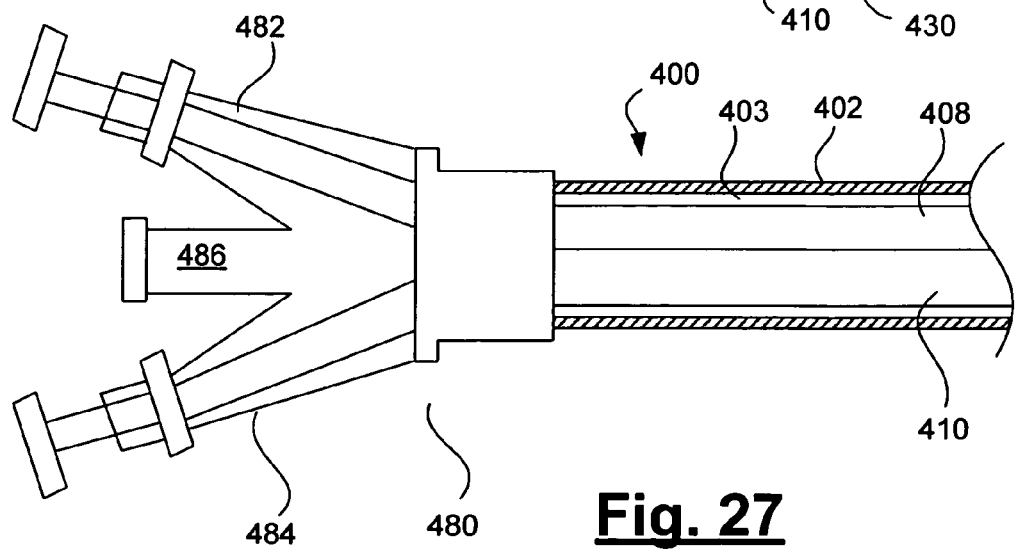
Fig. 27

```
┌─────────────────────────────────────┐
│   Advanced a catheter body having a first   │
│   needle and a second needle disposed therein │
│   to a treatment site, the first needle filled with │
│   a first agent and the second needle filled with │
│           a second agent            │
│                                     │
│                2802                 │
└─────────────────────────────────────┘
                   │
┌─────────────────────────────────────┐
│ At the treatment site, sequentially extend the first needle and │
│   the second needle from a distal tip of the catheter body │
│     (only one of the first needle or the second needle is │
│               extended at a time)                │
│                                     │
│                2804                 │
└─────────────────────────────────────┘
                   │
┌─────────────────────────────────────┐
│ Sequentially injecting the first agent and the second agent at the │
│                treatment site                │
│                                     │
│                2806                 │
└─────────────────────────────────────┘
                   ↑
                   │
                 2800
```

Fig. 28

DUAL NEEDLE DELIVERY SYSTEM

BACKGROUND

1. Field

The present invention pertains to for delivering multiple devices such as needles to a treatment site using one delivery apparatus.

2. Discussion of Related Art

A major component of morbidity and mortality attributable to cardiovascular disease occurs as a consequence of the partial or complete blockage of vessels carrying blood in the coronary and/or peripheral vasculature. When such vessels are partially occluded, lack of blood flow causes ischemia to the muscle tissues supplied by such vessel, consequently inhibiting muscle contraction and proper function. Total occlusion of blood flow causes necrosis of the muscle tissue.

Blood vessel occlusions are commonly treated by mechanically enhancing blood flow in the affected vessels. Such mechanical enhancements are often provided by employing surgical techniques that attach natural or synthetic conduits proximal and distal to the areas of occlusion, thereby providing bypass grafts, or revascularization by various means to physically enlarge the vascular lumen at the site of occlusion. These revascularization procedures involve such devices as balloons, endovascular knives (atherectomy), and endovascular drills. The surgical approach is accompanied by significant morbidity and even mortality, while the angioplasty-type processes are complicated by recurrent stenoses in many cases.

In some individuals, blood vessel occlusion is partially compensated by natural processes, in which new vessels are formed (termed "angiogenesis") and small vessels are enlarged (termed "arteriogenesis") to replace the function of the impaired vessels. These new conduits may facilitate restoration of blood flow to the deprived tissue, thereby constituting "natural bypasses" around the occluded vessels. However, some individuals are unable to generate sufficient collateral vessels to adequately compensate for the diminished blood flow caused by cardiovascular disease. Accordingly, it would be desirable to provide a method and apparatus for delivering agents to help stimulate the natural process of therapeutic angiogenesis to compensate for blood loss due to an occlusion in a coronary and peripheral arteries in order to treat ischemia. Delivering agents to a treatment site are needed in many other therapeutic treatments or procedures.

In some therapies, e.g., cardiovascular-related, cancer-related, and certain surgical or minimally-invasive therapies, it may be desirable to inject a treatment agent of or including a sustained release matrix intralumenally, intracardially, or intraventricularly. Unfortunately, however, it is generally difficult to retain the treatment agent at a desired treatment site. In cardiovascular-related therapies, for example, rarely is greater than 30 percent of the sustained release matrix retained at the injection site following such therapies. The loss of sustained release matrix generally occurs either during the initial injection or as a result of backflow from the needle site. The backflow from the needle site can occur due to an excessive amount of fluid required to deliver the matrix material, or, as the needle is removed from the injection site, the site does not seal before matrix material escapes. The consequences of matrix material escaping can be multifold depending on the interaction of the matrix and the surrounding blood or fluid.

The loss of matrix material and release can result in inconsistent dosage delivery. The inconsistency in dosage delivery in turn results in the delivery of the treatment agent that possibly will be at a dosage outside of the desired or optimum therapeutic window. In the case of arterial or ventricular treatment sites, a second response would occur if the sustained release matrix has thrombogenic effects, resulting in the formation of thrombosis that may have severe consequences in the arterial or ventricular region. Delivering an agent in a way that allows the agent to be retained at a treatment site is important.

Techniques are being developed for injections that can retain a treatment agent or agents, including a treatment agent of or including a sustained-release matrix at a treatment site. In many instances, it may be desirable to inject one or more agents and in many intakes, these agents once mixed, may form thick gel. In many other instances, it may be desirable to inject several agents that when allowed to react may form a gel matrix, thus, the agents need to be kept separate until injected at the treatment site. For instance, in some myocardial reinforcement therapy, two chemical components are to be injected to the injured myocardium. At the treatment site, the two components mix and form a gel to increase the wall thickness of the myocardium.

It is thus advantageous to have apparatuses and/or methods that enable delivering of device(s) to a treatment site that may benefit or enhance injection (or withdrawal) of agents at a treatment site.

SUMMARY

Aspects of the present invention pertain to apparatuses that enable delivery of more than one medical device such as needles, simultaneously or sequentially. In some aspects, the apparatus is configured to enable delivery of one medical device at a time. For instance, in some aspects, a delivery apparatus is configured to have one device retracted while another extended for delivery. In other aspects, more than one devices are extended at a time for delivery. The term delivery may mean injection, withdrawal, imaging, deploying, or otherwise delivering a device or device(s) to a particular treatment site. Although many embodiments of the present invention refer to a device or a medical device being a needle that can inject an agent into a patient, the embodiments described herein can similarly be applied for other devices such as a type of device that can are used to withdraw a fluid from a patient or other types of medical device such as an ablation device, an imaging device, a camera, a diagnostic device, a graft delivery device, and so forth.

One embodiment pertains to an apparatus that includes a catheter body having a first lumen and a second lumen extending therethrough. The first lumen is configured for a first device and the second lumen is configured for a second device to be disposed therein. A control handle is also coupled to the catheter body. The control handle includes a first control mechanism configured to control the first device and a second control mechanism configured to control the second device. A delivery path is provided in a distal portion of the catheter body. The delivery path is configured to enable separate introduction of the first device and the second device at a distal tip of the catheter body. The delivery path is configured to enable only one of the first device or the second device to be extended therethrough at any one time. The first device and the second device can be needles that can deliver an agent or agents to a treatment site.

Another embodiment pertains to an apparatus that includes a catheter body having a proximal section, a distal section, and at least a first lumen and a second lumen extending therethrough. The first lumen is configured for a first device and the second lumen is configured for a second device to be disposed therein. The first lumen and the second lumen are placed side-by-side to one another. There is no separating wall there between the first lumen and the second lumen at the distal section of the catheter body. A control handle is also coupled to the catheter body. The control handle includes a first control mechanism configured to control the first device and a second control mechanism configured to control the second device. The first lumen and the second lumen are configured to allow each of the first device and the second device to rotate therein and extend therefrom. The first and second devices can each be a needle that can deliver an agent or agents to a treatment site.

Another embodiment pertains to a method that includes advancing a catheter body having a first needle and a second needle to a treatment site. The catheter body has a proximal section, a distal section, and at least a first lumen and a second lumen extending therethrough. The first needle is inserted within the first lumen and the second needle is inserted within the second lumen. The method further includes, at the treatment site, sequentially extending the first needle and the second needle from a distal tip of the catheter body. Only one of the first needle or the second needle is extended at a time. Coupling to the catheter body is a control handle including a first control mechanism configured to control the first needle and a second control mechanism configured to control the second needle. Included at a distal section of the catheter body is a delivery path configured to enable separate introduction of the first needle and the second needle one at a time.

Another embodiment pertains to a method that includes advancing a catheter body having a first needle and a second needle to a treatment site. The catheter body has a proximal section, a distal section, and at least a first lumen and a second lumen extending therethrough. The first needle is inserted within the first lumen and the second needle is inserted within the second lumen. The method further includes positioning the first needle and the second needle such that the first needle and the second needle together form a sharp point. Then, a puncture is caused at the treatment site. At the treatment site, the method includes sequentially delivering the first needle and the second needle from a distal tip of the catheter body, wherein only one of the first needle or the second needle is delivered at a time. In one embodiment, an agent is delivered to the treatment site by each of the first needle and the second needle. Coupling to the catheter body is a control handle including a first control mechanism configured to control the first needle and a second control mechanism configured to control the second needle. In one embodiment, the first needle and the second needle are delivered simultaneously at the treatment site.

Another embodiment pertains to a method that includes advancing a catheter having a first needle and a second needle to a treatment site. The first needle and the second needle both extend out at a distal end of the catheter and the first needle and the second needle together form a sharp point at the distal end of the catheter. The method further includes rotating at least the first needle to orient a distal port of the first needle relative to a distal port of the second needle. The method further includes rotating the second needle to orient a distal port of the second needle relative to the distal port of the first needle.

Another embodiment pertains to an apparatus that comprises a catheter with an elongated shaft having a first lumen and a second lumen extending therethrough. The apparatus further comprises a distal section with a lumen in communication with a port in a distal end of the catheter and with the first lumen and the second lumen. The first lumen is configured for a first device and the second lumen is configured for a second device to be disposed therein. The apparatus further comprises a proximal adapter coupled to the elongated shaft with a first port in communication with the first lumen and a second port in communication with the second lumen.

BRIEF DESCRIPTION OF THE DRAWINGS

The present invention is illustrated by way of example and not limitation in the figures of the accompanying drawings, in which like references indicate similar elements and in which:

FIGS. 1-4 illustrate an exemplary embodiment of a delivery apparatus that can deliver multiple devices to a treatment site sequentially;

FIGS. 8-11 illustrate how to make an exemplary delivery apparatus;

FIGS. 23-27 illustrate exemplary configuration of multiple needles bonded together to be used with a delivery apparatus; and FIGS. 28-30 illustrate various exemplary embodiments of delivering multiple devices such as needles in accordance to embodiments of the present invention; and.

DETAILED DESCRIPTION

Figure 5:
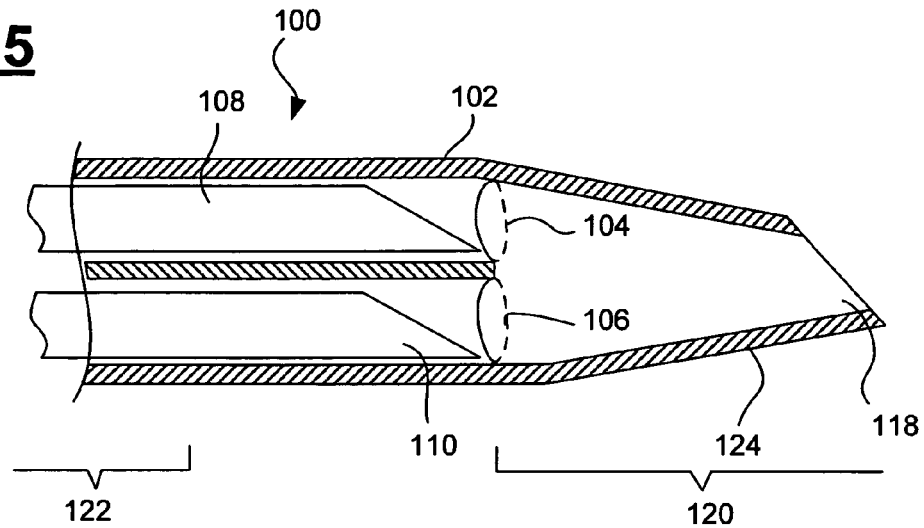
FIGS. 5-7 illustrate exemplary sequential delivery of multiple devices as a treatment site using the apparatus shown in FIGS. 1-4.

The exemplary embodiments of the present invention pertain to apparatuses and methods that can be used to deliver more than one device to a treatment site and examples of such devices include needles, imaging devices, ablation devices, cameras, diagnostic devices, graft delivery devices, and the like. The devices can be delivered at the treatment site simultaneously or sequentially. Various embodiments allow for delivery of the devices to substantially the same spot with minimal trauma to the entrance site.

In the following description, for purposes of explanation, numerous specific details are set forth in order to provide a thorough understanding of the present invention. It will be evident, however, to one skilled in the art, that the present invention may be practiced without these specific details. In other instances, specific apparatus structures and methods have not been described so as not to obscure the present invention. The following description and drawings are illustrative of the invention and are not to be construed as limiting the invention.

Embodiments of the present invention frequently refer to the term "treatment site." A treatment site may include, but is not limited to in or around a body tissue, a blood vessel or a body lumen such as a coronary blood vessel, a thoroscopic surgery site, an orthoscopic surgery site, and a laparoscopic surgery site. The treatment site may refer to a site where a therapeutic treatment is to be taken place at. For instance, an agent may be injected at the treatment site for a particular purpose or treatment. The treatment site may also refer to a site where a diagnostic procedure may occur or an imaging of the site may occur as desired or necessary for many procedures. Additionally, embodiments of the present invention frequently refer to the term "agent." An agent can be a treatment agent or a bio-agent component such as medication or drugs used in the prevention, alleviation, or cure of disease or injury, including, but not limited to agents directed to specific cellular binding sites and agents that induce inflammation.

Embodiments of the present invention pertain to a delivery apparatus that can perform a procedure such as delivering an agent to a treatment site, withdrawing a fluid or other substance from a treatment site, delivering or deploying a device at a treatment site, or performing other procedures at the treatment site. The delivery apparatus and method described herein are particularly suitable, but not limited to, local drug delivery in which an agent composition (possibly including multiple agents and/or a sustained-release agents) is introduced via multiple needle deliveries to a treatment site within a mammalian host (e.g., a patient). One suitable application for a delivery apparatus is that of a catheter device, including a needle delivery system. Suitable therapies that can benefit and utilize the exemplary delivery apparatus of the present invention include, but are not limited to, delivery of drugs for the treatment of arterial restenosis, therapeutic angiogenesis, or cancer treatment drugs/agents.

Various embodiments described herein can be used as a stand-alone injection needle/catheter during a surgical procedure such as an open chest surgery, an open heart surgery (e.g., Cabbage Coronary Bypass Graft (CABG)) procedure in which areas of the heart may be treated with, for example, growth factors, for affecting therapeutic angiogenesis, or incorporated into a catheter-based system to access locations that are commonly used in percutaneous translumenal coronary artery (PTCA) procedures. The exemplary apparatuses and methods may similarly be used in other surgical procedures such as cancer-related procedures (e.g., brain, abdomen, or colon cancer procedures or surgeries). Various embodiments described herein can be used in a laparoscopic procedures and in percutaneous procedures. Various apparatuses and methods described herein can also be used in conjunction with various catheter-related or endoscopy procedures that generally require minimal invasiveness to deliver a specific drug or growth factor into tissue. Examples of such procedures include, but are not limited to, orthoscopic surgery for joints (e.g., knee), laparoscopic surgery for the abdomen, and thoroscopic procedures related to chest injuries or treatments.

In one embodiment, a delivery apparatus 100 is described and is configured to allow multiple needles to inject one or more agents to a treatment site sequentially. With apparatuses such as the delivery apparatus 100, when more than one agents are to be injected, the agents can be injected substantially at the same spot, sequentially. For instance, two or more needles can be placed in the apparatus 100 as described herein, and the needles can be guided to relatively the same spot for injection, sequentially. The agents are kept separately until injected at the treatment site. The agents can be mixed together more efficiently at the treatment site. Furthermore, as can be seen from below, the apparatus 100 provides one delivery path to deliver multiple injections, with only one puncture is necessary since only one delivery path is required in the apparatus 100 thus minimizing injury or damages to injection site.

FIGS. 1-4 illustrate an exemplary apparatus 100 that can deliver multiple medical devices such as needles to a treatment site. Once delivered to the treatment site, the medical devices can perform the designated function such as injecting agents at the treatment site. The apparatus 100 includes a catheter body 102 having a first lumen 104 and a second lumen 106 extending therethrough. The first lumen 104 is configured for a first device 108 and the second lumen 106 is configured for a second device 110 to be disposed therein. A proximal handle 112 is also coupled to the catheter body 102 at a proximal portion 122 of the catheter body 102. The proximal handle 112 includes a first control mechanism 114 configured to control the first device 108 and a second control mechanism 116 configured to control the second device 110. A delivery path 118 is provided in a distal portion 120 of the catheter body 102. The delivery path 118 is configured to enable separate introduction of the first device 108 and the second device 110 at a distal tip 124 of the catheter body 102.

In one embodiment, both of the first device 108 and the second device 110 cannot enter the delivery path 118 at one time. In one embodiment, separate introduction of first device 108 and the second device 110 is achieved when the first device 108 and the second device 110 are introduced sequentially. The first device 108 and the second device 110 can be introduced sequentially where only one of the first device 108 or the second device 110 is extended through the delivery path 118 at a time In one embodiment, the first lumen 104 and the second lumen 106 extend as two separate lumens within the catheter body 102 for the most part of the catheter body 102 (FIGS. 2-3). The first lumen 104 and the second lumen 106 end, converge, or merge into a single lumen tubular section referred to as the delivery path 118 at the distal section 120 of the catheter body 102 (FIG. 4). The first device 108 travels independently within the first lumen 104 and the second device 100 travels independently within the second lumen 106. But when the devices 108 and 110 reaches the delivery path 118 at the distal section 120 of the catheter body, it is controlled such that only one of the device 108 or 110 is delivered or otherwise extended down the delivery path 118 and out from the distal tip 124.

Figure 6:
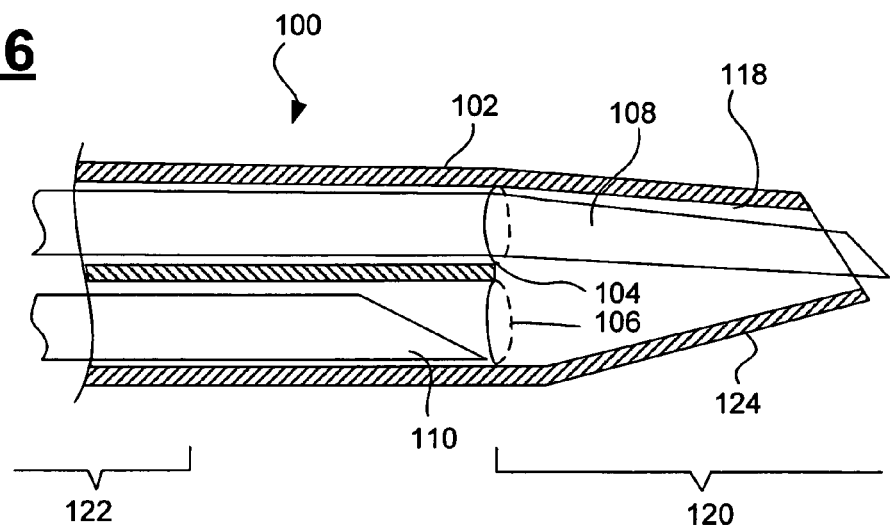

In one embodiment, during the delivery state, when not in use, or before the device 118 or 110 is delivered at the treatment site, the first device 108 rests in the first lumen 104 and the second device 110 rests in the second lumen 106 (FIG. 5). To separately introduce, deliver, or extend each device 108 or 110, the proximal handle 112 is manipulated to actuate either the device 108 or 110, one at a time, out of the distal tip 124. For instance, the proximal handle 112 is configured such that the first control mechanism 114 (FIG. 1), which is connected to the first device 108, can push on the first device 108 and advance the first device 108 from the first lumen 104 and into the delivery path 118 as shown in FIG. 6. While the first device 108 is being advanced, the second device 110 is stationary and not allowed to advanced. The delivery path 118 is also configured to enable only one of the device 108 or the device 110 to enter and extend therefrom, one at a time. After the first device 108 is delivered and ready to be withdrawn, the proximal handle 112, via the first control mechanism 114, retracts the first device 108 from the delivery path 118 and return the first device 108 to the first lumen 104. After the first device 108 is already delivered, the device 110 is delivered next, also by the proximal handle 112, via the second control mechanism 116 similar to how the first device 108 is advanced. While the second device 110 is being advanced, the first device 108 is stationary and not allowed to advanced. After the second device 110 is delivered and ready to be withdrawn, the proximal handle 112, via the second control mechanism 116, retracts the second device 110 from the delivery path 118 and returns the second device 110 to the second lumen 106.

In one embodiment, the first control mechanism 114 is coupled to or adhered to the first device 108 such that sliding the first control mechanism 114 along the proximal handle 112 can cause a corresponding extending/advancing or retracting of the first device 108 within the catheter body 102. Similarly, the second control mechanism 116 is coupled to or adhered to the second device 110 such that sliding the second control mechanism 116 along the proximal handle 112 can cause a corresponding extending/advancing or retracting of the second device 110 within the catheter body 102. The proximal handle 112 may include tracks (not shown) for the first control mechanism 114 and the second control mechanism 116 to slide along to manipulate the first device 108 and the second device 110, respectively. The control mechanisms 114 and 116 may be spring loaded to allow for automatic retraction of the devices once treatment is delivered.

In one embodiment, the proximal handle 112 includes an indicator 134 and an indicator 136 (FIG. 1), each indicator may function as a stopper for the control mechanisms 114 and 116, respectively, such that they will allow for controlling the extension distance of the devices 108 or 110 from the catheter body 102. The control mechanism 114 is prevented from moving pass the indicator 134 and as such, the device 108 is prevented from extending more distally than predetermined and indicated by the indicator 134. Similarly, the control mechanism 116 is prevented from moving pass the indicator 136 and as such, the device 110 is prevented from extending more distally than predetermined and indicated by the indicator 136. The indicators 134 and 136 may be positioned on the proximal handle 112 according to the predetermined extension distance that the devices 108 and 110 should be extended from the catheter body 102, and/or into the treatment site, and/or to reach the treatment site. The features provided by the indicators 134 and 136 are particularly useful when the devices 108 and 110 are needles that may have sharp points since the indicators 134 and 136 prevent unnecessary injury or puncture to the treatment site. Thus, the indicators 134 and 136 provide controls for the extension of the devices 108 ad 110, respectively.

Figure 7:
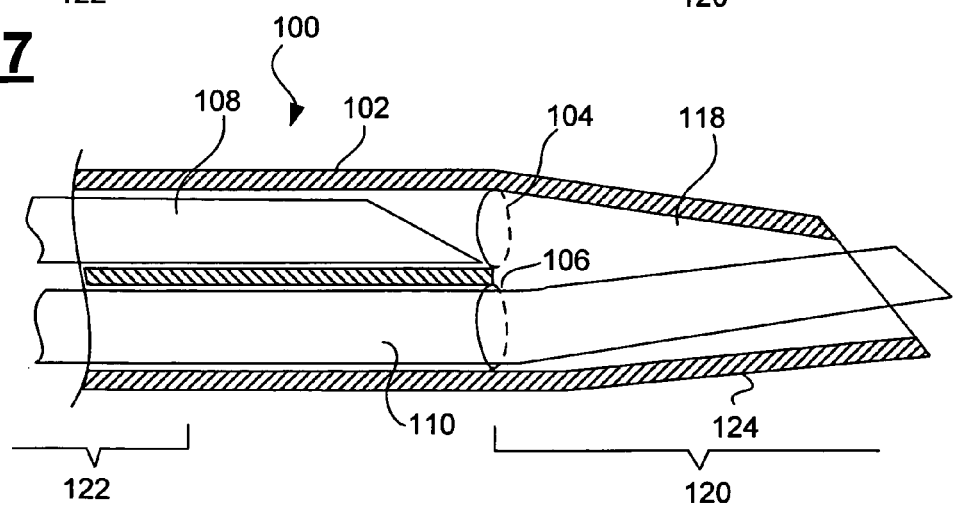

In one embodiment, the catheter body 102 ends at the distal tip 124 with a beveled point for easy entrance or puncturing into a treatment site. In one embodiment, the distal tip 124 is penetrated into the treatment site. The devices 108 and 110 each can be a needle filled with a bio-agent component. During delivery, the device 108 is in a retracted position and residing within the first lumen 104 and the device 110 is also in a retracted position and residing within the second lumen 106 as shown in FIG. 5. When ready for delivery, one needle at a time is advanced into the treatment site. As shown in FIG. 6, the first device 108 is extended out a predetermined distance from the distal tip 124. The device 108 has a beveled point as shown in FIG. 6. The bio-agent component in the device 108 is injected into the treatment site. After the injection, the device 108 is retracted back into the first lumen 104 as shown in FIG. 7. The device 110 is then extended out a predetermined distance from the distal tip 124 as shown in FIG. 7. The bio-agent component in the device 110 is injected into the treatment site.

In one embodiment, the delivery path 118 has an inner diameter with a tolerance just sufficient for one of the devices 108 or 110 to travel freely therethrough. For example, the inner diameter or inner dimension of the delivery path is smaller than the outer diameter or the outer dimension of the devices 108 and 110 combined. Thus, only one of the devices 108 or 110 can slidably extend through the delivery path 118 at a time. The delivery path 118 may be provided in a tapered end portion of the catheter body 102 (the distal portion 122 of the catheter body 102 being tapered), such that the delivery path 118 may have a smaller outer diameter than the rest of the catheter body 102. In one embodiment, the wall thickness of the catheter body 102 at the distal tip 124 is greater than the wall thickness for the rest of the catheter body 102. Thus, the lumen of the distal tip 124 (the delivery path 118) is smaller to allow for only one of the devices 108 or 110 to enter.

Each device 108 or 110 can be oriented to any particular direction or fixed to a pre-determined direction relative to each other and/or relative to the distal tip 124. In one embodiment, the direction or orientation of the devices 108 and 110 are controlled by the proximal handle 112 prior to the delivery. Each of the devices 108 and 110 may be oriented in a particular orientation and then fixed in that orientation after being disposed within the corresponding lumen 104 and 106. The devices 108 and 110 thus may be advanced or retracted but not rotated, in one embodiment. Alternatively, the proximal handle 112 can be configured to allow for adjustment of the direction or orientation of the devices 108 and 110 during the delivery, for example, a feature may be provided at the first control mechanism 114 and the second control mechanism 116 to rotate the device 108 or 110, respectively to a particular direction or orientation.

In one embodiment, the delivery path 118 and the distal tip 124 are configured to guide the devices 108 and 110 to one spot or one target at the treatment site so that the devices 108 and 110 can extend out to this particular one spot or one target location. In the present embodiment, the delivery path 118 and the distal tip 124 help aligning and directing both the devices 108 and 110 to substantially the same delivery site even though they are delivered sequentially. In such embodiment, two or more different agents that are to be mixed at a particular treatment site can be kept separate until delivery. When at the delivery site, the agents can be delivered substantially to the same spot at the treatment site. This allows for an efficient way to introduce agents into the treatment site and provide for optimal reaction. It is to be appreciated that the apparatus 100 is also useful for delivering other medical devices besides the needles with injections as described herein and above.

In one embodiment, the inner wall of the delivery path 118 is lined with a lubricious material (not shown) to facilitate the movement of the device 108 or 110 through the delivery path 118. The lining may also be comprised of a material that may not be easily damaged by a sharp tip that may be present in the device 108 or 110.

In one embodiment, the catheter body 102 is formed by welding or soldering two or more individual tubes (e.g., hypotubes or stainless steel hypotubes) together. Each of the first lumen 104 and the second lumen 106 may also be made of any suitable material such as polymers, co-polymers polyamides, polyolefins, polyurethane, nitinol, and the like. Constructions of tubes or structures with lumens therein are known in the art. As shown in FIG. 8, tubes 140 and 142 are provided which are then used to form the catheter body 102. Each of the tube 140 and 142 include, a lumen 144 and 146, respectively, extending therethrough. Each of the tubes 140 and 142 further includes a gradually ground taper ends 148 and 150, respectively. The gradually ground taper ends 148 and 150 are formed by cutting each of the tubes 140 and 142 at the distal ends such that these distal ends form somewhat half open tubes as shown in FIGS. 9A-9B. The catheter body 102 is then formed by having the tubes 140 and 142 welded, soldered or otherwise attached together as shown in FIGS. 10-11. The tubes 140 and 142 are welded soldered, or attached together at the gradually ground taper ends 148 and 150 forming the delivery path 118.

Once the tubes 140 and 142 are welded/soldered or attached together, the catheter body 102 is formed. In one embodiment, the catheter body 102 has a configuration that transforms from a dual lumen structure (formed by the two lumens 144 and 146) at the proximal region 122 into a single lumen distal region 120 formed by the two gradually ground taper ends 148 and 150 bonded together. The distal tip 124 of the catheter body 102 may be ground to a beveled point as shown in FIG. 10 for easy entrance into the treatment site. The catheter body 102 may have a Y-like shape where the first lumen 104 and the second lumen 106 are formed from the tubes 140 and 142, respectively. The first lumen 104 and the second lumen 106 are placed in two separate tracks which converge into the delivery path 118 at the distal region 120.

The catheter body 102 may include additional lumens (not shown) to accommodate, for example, a guidewire, an inflation balloon, a diagnostic device, and/or an imaging device. The catheter body 102 may also include more lumens similar to the first lumen 104 and the second lumen 106 for additional devices such as needles. In some instances, multiple needles (two or more) may be needed to inject multiple agents to a particular treatment site. In one embodiment, several lumens in the catheter body 102 converge into one path (e.g., the delivery path 118) as previously described.

In one embodiment, at the proximal end of each device 108 and 110 is an adaptor 160 and 162, respectively, for accommodating delivering of agents into the devices and ultimately to the treatment site (FIG. 1). The adaptors 160 and 162 each can be a molded female luer housing typically used to allow agent to be injected into the respective needles.

Embodiments such as those described above can be suitable for introducing a bioerodable and/or biocompatible gel into one or more locations, or parts of a patient. For example, a gel formed by a combination (mixing, contact, etc. . . . ) of an alginate and calcium chloride. Representatively, a 3.5 percent of an alginate solution may be introduced by a one cubic centimeters syringe at the adaptor 160 and through the device 108, which is a needle in the present example. Shortly before or after, a solution of calcium chloride may be introduced with a one cubic centimeter syringe at the adaptor 162 and through the device 110, which is also a needle in the present example. When the alginate and calcium chloride combine at the treatment site, the materials combine (mix, contact) to form a bioerodable gel. One example of a suitable amount of two material gel components for use in a cardiovascular treatment therapy is approximately 200 microliters of alginate solution and one milliliter calcium chloride. Excess calcium chloride may flush through the patient as a saline solution. It is to be noted that the agents can be injected sequentially or simultaneously.

In an alternative embodiment, instead of having a proximal handle 112 which includes or incorporates both the first control mechanism 114 and the second control mechanism 116 to control movements of the devices 108 and 110, respectively, there may be one separate proximal control device each including the control mechanism for each of the devices 108 and 110.

Figure 12A:
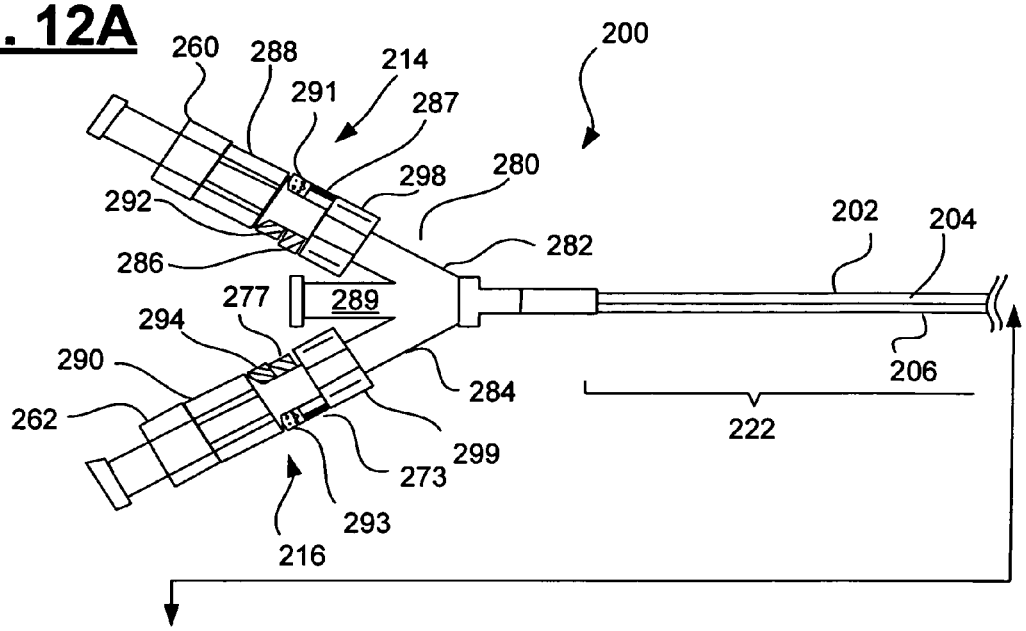
FIGS. 12A-12B and 13 illustrate an exemplary embodiment of a delivery apparatus that can deliver multiple devices.
Figure 12B:
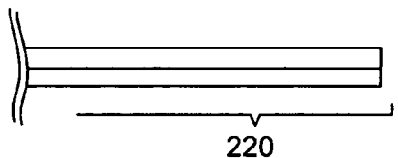
Figure 14:
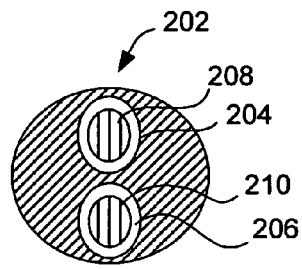
FIGS. 14-16 illustrate in more details the apparatus shown in FIGS. 12A-12B and 13.
Figure 15:
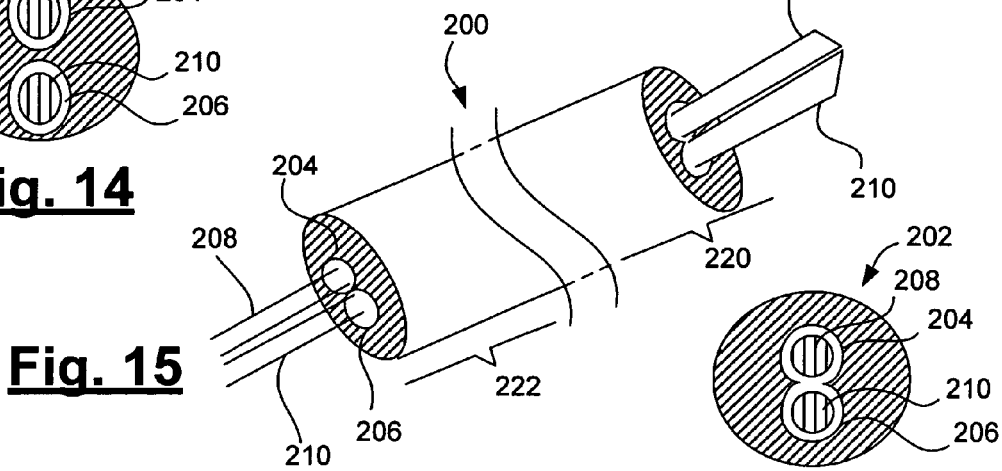
Figure 16:
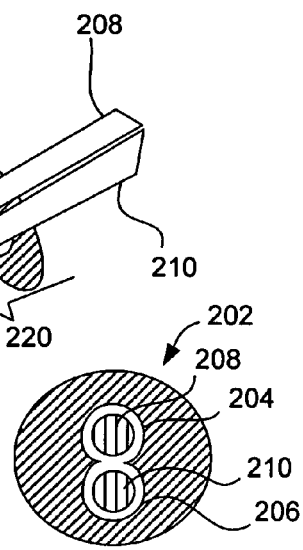

Another embodiment (FIGS. 12-16) pertains to an apparatus 200 that includes a catheter body 202 having a proximal section 222, a distal section 220, and at least a first lumen 204 and a second lumen 206 extending therethrough (FIGS. 12A-12B and 15). The first lumen 204 is configured for a first device 208 and the second lumen 206 is configured for a second device 210 to be disposed therein. In one embodiment, the first device 208 and the second device 210 are needles that can deliver an agent or agents to a treatment site. Of course, the devices 208 and 210 can also be other devices as previously mentioned. At the proximal section 222, the first lumen 204 and the second lumen 206 are placed adjacent to one another like two parallel tubes running within a catheter body 202 (FIGS. 14-15). At the distal section 220, the first lumen 204 and the second lumen 206 are also placed adjacent to one another but the lumens together form an 8-like cross section (FIGS. 15-16). Thus, the first lumen 204 and the second lumen 206 are placed side by side, longitudinally adjacent, or adjacent and very close to each other with each lumen having a section adjoining the other such that at this section, the lumens have no separating wall between them (see cross section in FIG. 16). The first lumen 204 and the second lumen 206 may fuse together to form one lumen with a cross-sectional shape similar to a number 8. The catheter body 202 may have other lumens to accommodate other devices such as guidewires or imaging devices.

In one embodiment, the catheter body 202 may have configuration of a tube with multi-lumens therewithin for the entire length of the catheter body 202. In the present embodiment, an adaptor 280 is coupled to the proximal end of the catheter body 202 (FIG. 12A). The adaptor 280 includes at least two ports 282 and 284 wherein each of the ports 282 and 284 communicates to one of the lumens 204 or 206. In one embodiment, the devices 208 and 210 are inserted through the ports 282 and 284, respectively, and into the respective first lumen 204 and second lumen 206. The adaptor 280 also includes an additional port 289 which can be used for venting, for inserting additional devices, or other purposes.

In one embodiment, the adaptor 280 is configured to be a proximal control handle that is coupled to the proximal end of the catheter body 202. The control handle couples to a first control mechanism 214, which is configured to control the first device 208, and a second control mechanism 216, which is configured to control the second device 210. The first control mechanism 214 is further coupled to or attached to the first device 208 such that the first control mechanism 214 is able to actuate, rotate, or extend the first device 208 to a particular orientation or direction. The first lumen 204 is sized so as to allow the first device 208 to rotate therein as well as extend therefrom. Similarly, the second control mechanism 216 is further coupled or attached to the second device 208 such that the second control mechanism 216 is able to actuate, rotate, or extend the second device 210 to a particular orientation or direction. The second lumen 206 is also sized so as to allow the second device 210 to rotate therein as well as extend therefrom.

In one embodiment, to control rotation of the first device 208, the first control mechanism 214 is provided with a rotation knob 288 with an indicator 291 and an indicator 292. The first control mechanism 214 is also provided with a stationary knob 298 with an indicator 286 and an indicator 287. When the rotation knob 288 is rotated or turned, the first device 208 is accordingly rotated or turned. The indicators 291 and 292 work in conjunction with the indicators 286 and 287 to indicate to an operator the orientation of the first device 208. For instance, when the rotation knob 288 is turning or rotating to rotate the first device 208, the indicators 291 and 287 may line up so as to limit the rotation of the first device 208 and the indicator 292 may line up with the indicator 286 to perform similar function. When the indicators line up, the operator is informed of the position of the first device 208 upon the rotation. The indicators 291 and 287 and the indicators 292 and 286 thus may function not only to indicate the orientation of the first device 208 but also to limit over rotation of the first device 208. With the indicators, the first device 208 does not easily get over rotated and its rotation can be controlled with the rotation knob 288.

Similarly, embodiment, to control rotation of the second device 210, the second control mechanism 216 is provided with a rotation knob 290 with an indicator 293 and an indicator 294. The second control mechanism 216 is also provided with a stationary knob 299 with an indicator 276 and an indicator 277. When the rotation knob 290 is rotated or turned, the second device 210 is accordingly rotated. The indicators 294 and 293 work in conjunction with the indicators 277 and 276 to indicate to an operator the orientation of the second device 210. For instance, when the rotation knob 290 is turning or rotating to rotate the second device 210, the indicators 293 and 276 may line up so as to limit the rotation of the second device 210 and the indicator 294 may line up with the indicator 277 to perform similar function. When the indicators line up, the operator is informed of the position of the second device 210 upon the rotation. The indicators 293 and 276 and the indicators 294 and 277 thus may function not only to indicate the orientation of the second device 210 but also to limit over rotation of the second device 210. With the indicators, the second device 210 does not easily get over rotated and its rotation can be controlled with the rotation knob 290.

Figure 13:
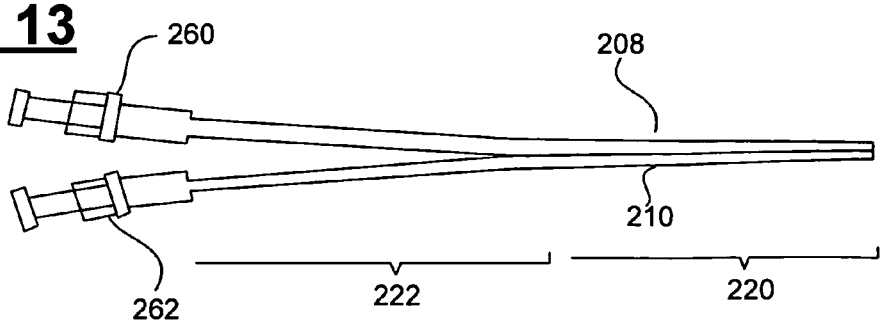

FIG. 13 illustrates an exemplary embodiment of the devices 208 and 210 and that can be inserted into the delivery apparatus 200 and delivered to a treatment site. In one embodiment, the devices 208 and 210 are each a needle that can inject an agent or agents into the treatment site. In one embodiment, at the proximal end of each device 208 and 210 is an adaptor 260 and 262, respectively, for accommodating delivering of agents into the devices and ultimately to the treatment site. The adaptors 260 and 262 each can be a molded female luer housing typically used to allow agent to be injected into needles. In one embodiment, the first device 208 is inserted into the adaptor 280 at the port 282 and into the lumen 204 of the catheter body 202. The second device 210 is inserted into the adaptor 280 at the port 284 and into the lumen 206 of the catheter body 202.

In one embodiment, the delivery apparatus 200 is used to deliver a bio-agent component to a treatment site 301. In the present embodiment, the first device 208 is a first needle 308 and the second device 210 is a second needle 310, which are used to inject agents to the treatment site 301 that form the desired bio-agent component upon mixing at the treatment site 301 (FIG. 17-22). In one embodiment, the bio-agent component includes a first agent 318 and a second agent 320. The first agent 318 is carried inside the first needle 308 and the second agent 320 is carried in the second needle 310. The first injection needle 308 and the second injection needle 310 each has a beveled tip (312 and 314, respectively) typically seen in a needle. In one application, the first agent 318 and the second agent 320 form a gel matrix once they are mixed together. Therefore, it is desirable not to have the two agents mixed before injection into the treatment site 301. It is typically more difficult to inject a gel component through a lumen of a small needle. Furthermore, it is desirable to keep the two agents completely separate until the treatment site 301 since any accidental injection of one agent into the other component may cause clogging in the needles. To ensure injecting the two agents into the same spot for mixing purpose and to prevent injection one agent into the adjacent needle lumen causing clogging, the injection can be done in series.

Figure 17:
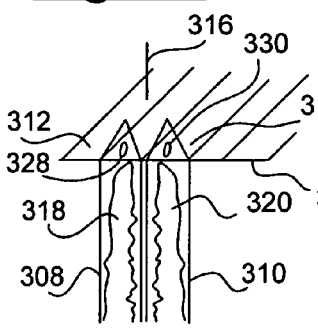
FIGS. 17-22 illustrate exemplary configurations of two needles placed in a delivery apparatus in accordance with embodiments of the present invention.

In one embodiment, during delivery and at the fist puncture/entrance into the treatment site 301, the first injection needle 308 and the second injection needle 310 are positioned so that together the beveled distal tips 312 and 314 of the needles 308 and 310 form one sharp point as shown in FIG. 17. The first needle 308 and the second needle 310 may be rotated so that they have sides pressed against each other and that their beveled tips together formed the sharp point. The first needle 308 and the second needle 310 may have sides that rest against each other. As previously discussed in one embodiment, at the distal section 220, the first lumen 204 and the second lumen 206 may fuse together to form a delivery path. This path allows the first needle 308 and the second needle 310 to rest against each other. A centerline 316 is formed between the distal tip 312 and the distal tip 314. The centerline 316 may be seen as the contact line between the two needles 308 and 310. At this point, the beveled distal tip 312 has a distal opening 328 facing away form the centerline 316. Similarly, the beveled distal tip 314 has a distal opening 330 facing away form the centerline 316.

Figure 18:
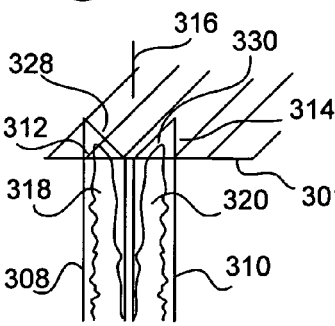
Figure 19:
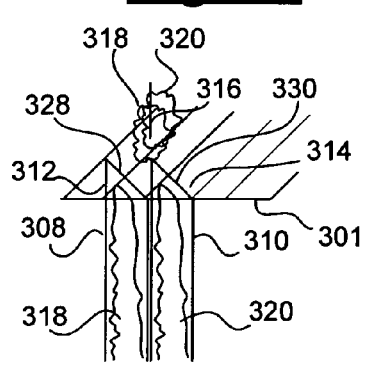

Next, either the first agent 318 or the second agent 320 is injected into the treatment site 301. In one example, the second agent 320 is injected first followed by the first agent 318 as illustrated in FIGS. 18-19. In FIG. 18, to deliver the second agent 310 into the treatment site 301 from the second injection needle 320, the injection needle 310 is rotated (while the first injection needle 308 is stationary) to have the needle distal opening 330 facing the centerline 316. Then, the second agent 320 is injected into the treatment site 301. Since the first injection needle 308 still has its distal opening 328 facing away from the centerline 316, the second agent 320 is prevented from entering into the first injection needle 308. The two agents are thus kept separate until injected into the treatment site 301.

Next and once the first injection is done, the second injection needle 310 is rotated with its beveled distal opening 330 facing away from the centerline 316 as shown in FIG. 19. The second injection needle 310 is rotated back to its initial state. Then, the first injection needle 308 is rotated with its beveled distal opening 328 facing the centerline 316 as shown in FIG. 19. Similar to above, while the first injection needle 308 is rotated, the second injection needle 310 is stationary. The first agent 318 is then injected into the treatment site 301 substantially in the same spot where is the second agent 320 is injected into. The injection pressure will cause the two agents to mix and such mixing initiates the therapeutic reaction of forming a gel matrix in the treatment site. It may not be necessary to rotate the second needle 310 back to its initial state prior to the delivery of the first agent 318. Thus, after the second agent 320 is injected as shown in FIG. 18, the first needle 308 is rotated to have its beveled distal opening 328 facing the center line and the first agent 318 is injected. Both needles may be withdrawn without being rotated back to their initial delivery state.

In another embodiment, the first agent 318 is injected first into the treatment followed by the second agent 320. The process described would be reversed. Thus, the first injection needle 308 is rotated to face the centerline and the first agent 318 is injected. The first injection needle 308 is rotated back to the initial position. Then, the second injection needle 310 is rotated to face the centerline and the second agent 320 is injected.

It is to be noted that the two injection needles 308 and 310 can be rotated to form any angle from each other, for example, to face each other or to form a 180-degree angle with each other with respect to their distal openings.

In one embodiment, the delivery apparatus 200 is moved to a different treatment site and the injection process repeated for additional injections.

Figure 20:
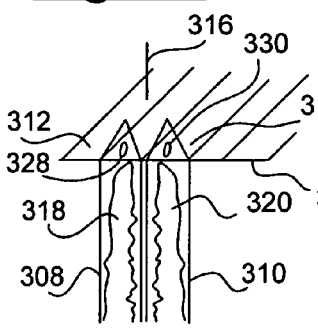
Figure 21:
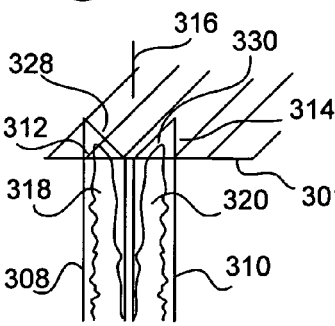

In some embodiments, the agents are injected simultaneously into the treatment site 301. As illustrated in FIG. 20, after the initial entrance as shown in FIG. 17, the first injection needle 308 and the second injection needle 310 are rotated such that the distal openings 328 and 320 are facing the same direction. The first agent 318 and the second agent 320 are then injected into the treatment site 301 simultaneously or at the same time. As illustrated in FIG. 21, in another example, after the initial entrance as shown in FIG. 17, the first injection needle 308 and the second injection needle 310 are rotated such that the distal openings 328 and 320 are facing each other. The first agent 318 and the second agent 320 are then injected into the treatment site 301 simultaneously or at the same time.

Figure 22:
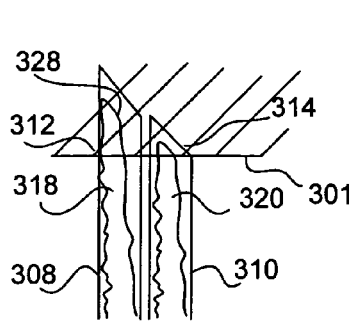

In yet another embodiment, the first injection needle 308 and the second injection needle 310 are positioned such that one needle is on top of another needle as illustrated in FIG. 22. For instance, as shown in FIG. 22, the second injection needle 310 is placed on top of the fist injection needle 308. The needles are positioned such that they still form one sharp point for easy entrance into the treatment site 301. In this configuration, the orientations of the needles are limited or are fixed. Thus, from the entrance point to the injection point, the trauma caused to the treatment site 301 is minimized.

In other embodiments, instead of two needles, there may be three or more needles. When more needles are used, to maintain a sharp point at the distal needle tip, diameter of the needles should be smaller. Additionally, not all of the devices disposed in the delivery apparatus 200 need to be the same, e.g., not all devices are needles. A combination of different devices can be delivered to a treatment site using the delivery apparatus 200.

In any of the embodiments herein, each needle can be coated to further prevent sticking with the agent that is placed within the needle to be delivered to the treatment site. It is be to noted that the agents injected into the treatment site need not be the kind that need mixing as previously discussed. Instead, the agents can be components with different therapeutic effects that need to be delivery to the vicinity of each other.

FIGS. 23-26 illustrate other exemplary embodiments of the devices that can be used for multiple injections or multiple device delivery at one treatment site. FIG. 27 illustrates an exemplary delivery apparatus 400 that can be used in conjunction with the devices shown in FIGS. 23-26. In these embodiments, instead of having rotatable devices or needles, the devices or needles can be welded together to the desired orientation. The delivery of these devices can also be done simultaneously or optionally, sequentially.

The delivery apparatus 400 (FIG. 27) is similar to the apparatus 200 previously described except that the multiple devices are bonded, welded, or otherwise attached together and they are disposed within one lumen of the catheter body. The apparatus 400 includes a catheter body 402 having a lumen 403 extending therethrough. A proximal adaptor 480 is coupled to the proximal end of the catheter body 402. The proximal adaptor 480 may also include other controlling components or handles to individually control the devices in the apparatus 400 similarly to previously described in the apparatus 200 or 100. The adaptor 480 also includes a first port 482 and a second port 484. Additional port such as port 486 may also be included for other purposes or other devices. As before, a first device 408 is inserted through the first port 482 and a second device 410 is inserted through the second port 484. Prior to the adaptor 480 point, each of the device 408 and 410 is kept separate. The remainder portions of the each of the devices 408 and 410 (the portions within the catheter body 402) are welded or bonded together as shown in FIGS. 23-26.

Unlike the previous embodiments where each device is kept separate in its own lumen provided within the catheter body, in the embodiments shown in FIGS. 23-27, the devices are welded or bonded together and placed in one lumen provided in the catheter body 402. In FIG. 23, the first device 408 and the second device 410 are bonded together to form a device bundle 433, 437, or, 439. The device bundle can be placed within the catheter lumen 403 of the catheter body 402 shown in FIG. 27. In one embodiment, the first device 408 and the second device 410 are each a needle having a lumen extending therethrough for agent delivery. The first device 408 includes a distal opening 428 and the second device 410 includes a distal opening 430. The distal openings 428 and 430, each may be beveled. The device bundle is thus like a needle with multiple lumens with each lumen dedicated for an agent to be dispensed therethrough. In one embodiment as shown in FIG. 23, the device bundle 433 has the first device 408 and the second device 410 positioned so that each distal opening 428 and 430 of the devices 408 and 410, respectively, are facing in the same direction. The device bundle 433 has only one sharp point 435 making it easy and less traumatic for the treatment site at the entrance or the puncturing site, in one embodiment.

In FIG. 24, the first device 408 and the second device 410 are bonded together to form a device bundle 437. The device 437 is placed within the catheter lumen 403 of the catheter body 402 shown in FIG. 27. The first device 408 and the second device 410 are each a needle having a lumen extending therethrough for agent delivery. The first device 408 includes the distal opening 428 and the second device 410 includes the distal opening 430. The device 437 is also like a needle with multiple lumens. The first device 408 and the second device 410 are positioned so that each distal opening 428 and 430 of the devices 408 and 410, respectively, are facing in the same direction and one device is placed on top of the other. As shown in FIG. 24, the first device 408 with the opening 428 is placed on top of the second device 410 with the opening 430. The device 437 also has only one sharp point 435 making it easy and less traumatic for the treatment site at the entrance or the puncturing site, in one embodiment.

In FIG. 25, the first device 408 and the second device 410 are bonded together to form a device bundle 439. The device 439 is placed within the catheter lumen 403 of the catheter body 402 shown in FIG. 27. The first device 408 and the second device 410 are each a needle having a lumen extending therethrough for agent delivery. The first device 408 includes the distal opening 428 and the second device 410 includes the distal opening 430. The device 439 is also like a needle with multiple lumens. Additionally, the device 439 is also like a needle with multiple sharp points 441. The first device 408 and the second device 410 are positioned so that each distal opening 428 and 430 of the devices 408 and 410, respectively, are somewhat facing each other and/or facing the same direction. The distal opening 428 and 430 of the devices 408 and 410 of the device 439 captures the treatment site between them. In the embodiments where the devices 408 and 410 are each a needle, the agents to be delivered to the treatment site is captured between the openings 428 and 430 minimizing unnecessary dispersion and enhancing physical contact of the agents for providing efficient mixing. FIG. 26 illustrates a device similar to the device 439 in FIG. 25 except that the first device 408 and the second device 410 are positioned with a different angle and the openings 428 and 430 are directly opposing one another.

Embodiments with first device and the second device bonded together as previously discussed, provide some advantages when the devices are needles. The bonding of the needles together allow for multiple and separate introduction of agents at a treatment site while keeping the agents separate until injection. Additionally, binding the needles together limit orientation or rotation which may reduce the trauma or injury to the treatment site. Further, less steps is required to perform multiple injections, for instance, no rotation of the needle is necessary after injection of each agent from each needle. Further yet, binding of the needles together minimize the gaps that may be present in other embodiments thus minimizing back flow of agents.

Embodiments such as those described above in FIGS. 12-27 can be suitable for introducing a bioerodable and/or biocompatible gel into one or more locations or parts of a patient. For example, a gel formed by a combination (mixing, contact, etc. . . . ) of an alginate and calcium chloride. Representatively, a 3.5 percent of an alginate solution may be introduced by a one cubic centimeters syringe through the first device 208, which is a needle in the present example. A solution of calcium chloride may be introduced with a one cubic centimeter syringe through the second device 210, which is also a needle in the present example. When the alginate and calcium chloride combine at the treatment site, the materials combine (mix, contact) to form a bioerodable gel. One example of a suitable amount of two material gel components for use in a cardiovascular treatment therapy is approximately 200 microliters of alginate solution and one milliliter calcium chloride. Excess calcium chloride may flush through the patient as a saline solution. It is to be noted that the agents can be injected simultaneously or sequentially.

FIG. 28 illustrates an exemplary method 2800 of delivering a device, including injecting an agent carried by the device such as a needle, to a treatment site. The same method can be used to deliver other devices that does not involve injection such as an imaging device, a flow or pressure measuring device, or other devices that are used to withdraw fluids or substances from a patient. In method 2800, at box 2802, a catheter having a first needle and a second needle disposed therein is advanced to a treatment site. The first needle is filled with a first agent and the second needle is filled with a second agent as previously discussed. At box 2804, at the treatment site, the first needle and the second needle are sequentially extended from a distal tip of the catheter. Only one of the first needle or the second needle is extended at a time. At box 2806, the first agent and the second agent are sequentially injected at the treatment site. For instance, to inject the first agent, the first needle is extended while the second needle is not. The first agent is injected into the treatment site. After the first agent is injected, the first needle is retracted and the second needle is extended. The second agent is then injected into the treatment site.

In one embodiment, the catheter used in the method 2800 has a proximal section, a distal section, and at least a first lumen and a second lumen extending therethrough. The first needle is inserted within the first lumen and the second needle is inserted within the second lumen. Coupled to the catheter is a control handle including a first control mechanism configured to actuate the first needle and a second control mechanism configured to actuate the second needle. A distal section of the catheter includes a delivery path configured to enable separate introduction of the first needle and the second needle one at a time.

Figure 29:
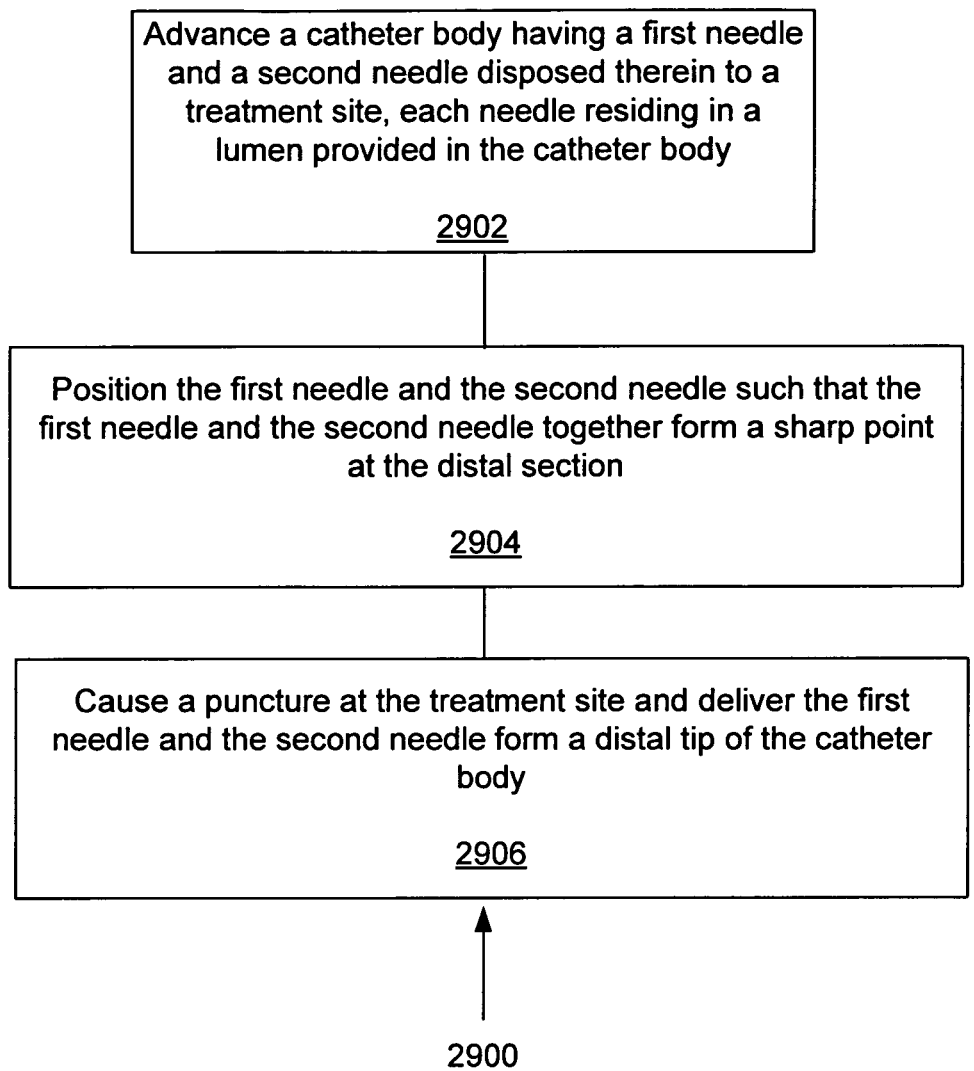

FIG. 29 illustrates an exemplary method 2900 of delivering a device, including injecting an agent carried by the device such as a needle, to a treatment site. In method 2900, at box 2902, a catheter having a first needle and a second needle disposed therein is advanced to a treatment site. The first needle is filled with a first agent and the second needle is filled with a second agent as previously discussed. At box 2904, the first needle and the second needle are positioned such that the first needle and the second needle together form a sharp point at the distal section. At box 2906, a puncture is created at the treatment site and the first needle and the second needle are delivered from a distal tip of the catheter body. Delivering the needles also includes injecting the agents within the needles into the treatment site either sequentially or simultaneously.

In one embodiment, the first agent and the second agent are delivered sequentially with only one of the first needle or the second needle injecting the agent into the treatment site one at a time. In one embodiment, prior to delivering, a distal opening of the first needle and a distal opening of the second needle are position so that they face away from a center line between the first needle and the second needle. Next, while the second needle is stationary, the first needle is rotated to have the distal opening of the first needle facing the center line. The first agent is then injected at the treatment site. After the first agent is injected, the first needle is rotated back or rotated to have the distal opening of the first needle facing away from the center line. Then, while the first needle is stationary, the second needle is rotated to have the distal opening of the second needle facing the center line. The second agent is then injected at the treatment site. After the second agent is injected, the second needle is rotated back or rotated to have the distal opening of the second needle facing away from the center line.

In another embodiment, the first agent and the second agent are delivered simultaneously into the treatment site. In one embodiment, prior to delivering, a distal opening of the first needle and a distal opening of the second needle are positioned so that they are facing away from a center line between the first needle and the second needle. Such positioning gives the needles one sharp point to facilitate easy entrance into the treatment site. Next, the first needle and the second needle are rotated to have the distal opening of the first needle and the second needle facing the center line. Then, the first agent and the second agent are injected simultaneously and independently at the treatment site. In another embodiment, instead of having the distal opening of each of the first needle and the second needle facing each other, the distal openings are facing the same direction toward the treatment site. Then, the first agent and the second agent are injected simultaneously and independently at the treatment site.

Figure 30:
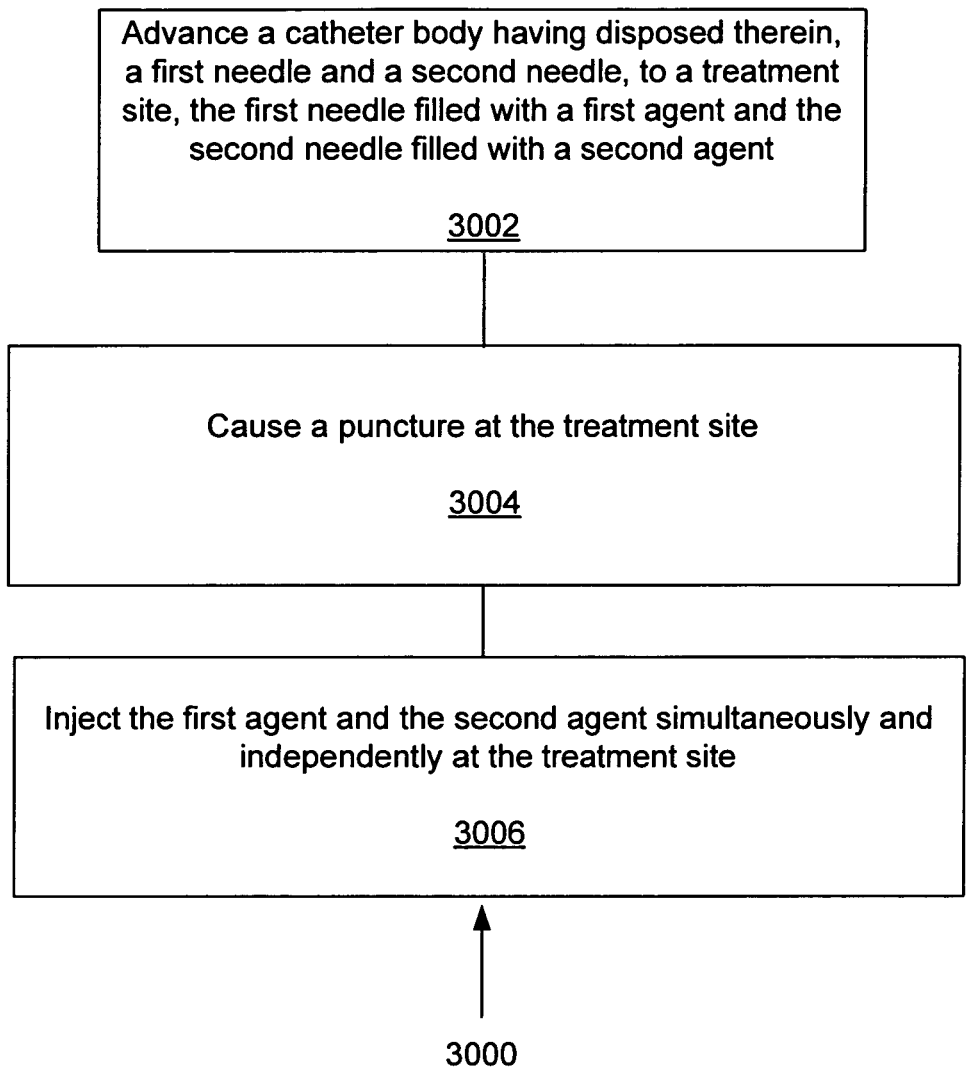

FIG. 30 illustrates an exemplary method 3000 of delivering a device, including injecting an agent carried by the device such as a needle, to a treatment site. In method 3000, at box 3002, a catheter having disposed therein, a first needle and a second needle bonded together, to a treatment site. Each of the first needle and the second needle has a distal opening and a lumen extending therethrough. A puncture is created at the treatment site. The first agent and the second agent are injected simultaneously and independently at the treatment site. In one embodiment, the first needle and the second needle are bonded together with one beveled tip that includes both the distal openings of the first needle and the second needle therein. In another embodiment, the first needle and the second needle are bonded together with the distal opening the first needle and the distal opening of the second needle facing each other.

Figure 31A:
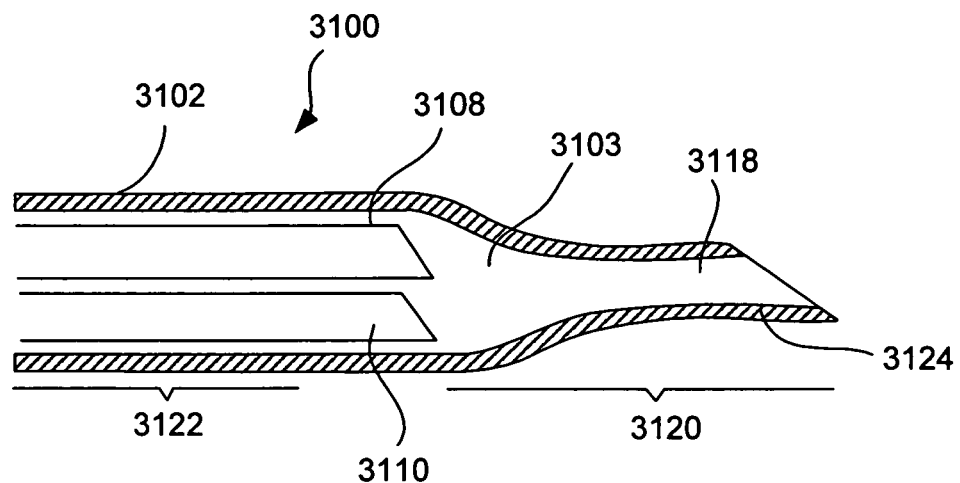
FIGS. 31A-31B illustrate exemplary embodiment of a delivery apparatus that can deliver multiple devices to a treatment site sequentially.

FIG. 31A illustrates yet another embodiment of a catheter apparatus 3100 that can deliver multiple devices (e.g., needles) to a treatment site. As previously mentioned, multiple needles each having an agent can be delivered to a treatment site. At the treatment site, the agents can be delivered simultaneously or sequentially. The catheter apparatus 3100 is similar to the previous catheter apparatuses (e.g., 100, 200, and 400) except that the multiple devices can be disposed only in one lumen that extends from the proximal portion of the distal portion of the catheter apparatus 3100.

Similar to previously described, the apparatus 3100 includes an elongated catheter shaft or body 3102 for the devices to be disposed therethrough. The catheter shaft 3102 has a lumen 3103 extending therethrough. The lumen 3103 accommodates a first device 3108 (e.g., a needle) and a second device 3110 (e.g., a needle) to be disposed therein. The catheter shaft 3102 has a proximal section 3122 and a distal section 3120, wherein the distal section 3120 of the lumen 3103 is narrower than the proximal section 3122. In one embodiment, at the distal section, the lumen 3103 is tapered so that only one of the device 3108 or 3110 can be extended therethrough at one time. There is no gap or substantially no gap between the first device 3108 and the second device 3110 at the distal section 3122 of the catheter 3102. Alternatively, there is no gap or substantially no gap between the first device 3108 and the second device 3110 throughout the lumen 3103 of the catheter 3102. The devices 3108 and 3110 are placed so close to each other such that there is no wall separating the devices. In one embodiment, the devices 3108 and 3110 are not fixed or attached to each other and only placed side-by-side. Each device is capable of rotation without affecting the other.

In other aspects, the apparatus 3100 is similar to the apparatuses 100, 200, and 400 previously described except for the single lumen at the proximal section of the catheter body 3102. Similar proximal handles or control devices can be coupled to the catheter body 3102 at the proximal end to allow for independent controlling of the devices 3108 and 3110. In one embodiment, a proximal adapter is coupled to the elongated shaft with a first port to be in communication with the first device 3108 and a second port in communication with the second device 3110 similar to previously described.

Figure 31B:
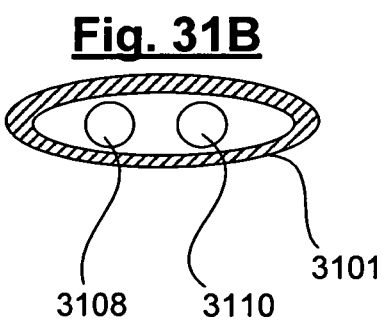

In one embodiment, the lumen 3103 is oval-shape lumen throughout the catheter body 3102 as shown in FIG. 31B. The lumen 3103 may also has a figure-8-like shape or cross section similar to shown in FIG. 16. In such event, the lumen 3103 may be formed by fusing, merging, or welding multiple lumens or tubes together to form the lumen 3103 such that the devices 3108 and 3110 can be disposed with no separating wall between them.

In one embodiment, at the distal section 3120, the lumen 3103 is configured to only be able to accommodate only one device at a time. Thus, as shown in FIG. 31A, only the device 3108 or 3110 can extend from the lumen 3103 at the distal section 3120 at a time. The lumen 3103 may be tapered or narrowed so that the inner dimension of the lumen 3103 is smaller than the outer dimensions of both the device 3108 and the 3110 combined.

In an alternative embodiment, the lumen 3103 at the distal section 3120 has an oval shape to restrict the movement of the devices 3108 or 3110 but to allow rotation of each device. In this embodiment, the distal section 3120 can accommodate both the devices 3108 and 3110 at one time.

Any of the embodiments discussed herein can accommodate a flushing agent to be flushed therethrough during a delivery process. There is a concern for the injected agent(s) to back flow into the flow blow (e.g., either to the heart chamber or the blood vessel). It is believed that flushing the treatment site with an agent such as heparin may block the process of the back-leaked agent from forming thrombus. An apparatus of the embodiments of the present invention may be configured to allow flushing through a lumen or lumens of the catheter. An adaptor may be attached to the lumen on the proximal end or as a part of the proximal handle (e.g., via the port 289 of the apparatus 200 or the port 486 of the apparatus 400). During injection and/or post injection right after withdrawal of the needle from the puncture site, a heparin solution is injected around the puncture site to prevent thrombus formation. This injection lumen can also be used to inject contrast or other agent such as for the purpose of confirming the puncturing site.

It is to be understood that even though numerous characteristics and advantages of various embodiments have been set forth in the foregoing description together with details of structures and function of the various embodiments, this disclosure is illustrative only. Changes may be made in detail, especially matters of structure and management of parts, without departing from the scope of the various embodiments.

The invention claimed is:

1. An apparatus comprising:
a catheter body having a first lumen and a second lumen extending therethrough, the first lumen configured for a first device and the second lumen configured for a second device to be disposed therein;
a control handle coupled to the catheter body, the control handle including a first control mechanism configured to control a movement of the first device, the first control mechanism including a first rotation knob operable to rotate the first device;
a separate second control mechanism configured to control a movement of the second device, the second control mechanism including a second rotation knob operable to rotate the second device;
a first indicator stop operable to limit a distal extension distance movement of the first control mechanism;
a separate second indicator stop operable to limit a distal extension distance movement of the second control mechanism; and
a delivery path provided in a distal portion of the catheter body, the delivery path configured to enable separate introduction of the first device and the second device at a distal tip of the catheter body,
wherein the delivery path is configured such that only one of the first device or the second device is actuated at a time, or is configured such that the delivery path inner dimension is smaller than an outer dimension of the first device and the second device combined, or is configured such that the delivery path is too small to accommodate both the first device and the second device at one time.

2. The apparatus of claim 1 wherein the first lumen and the second lumen are two separate lumens running parallel to one another through the catheter body and wherein the first lumen and the second lumen fuse at one section of the catheter body to form the delivery path.

3. The apparatus of claim 1 wherein the catheter body has a Y-like shape wherein the first lumen and the second lumen are placed into two separate tracks and converge into the delivery path at the distal portion of the catheter body.

4. The apparatus of claim 1 wherein the first control mechanism is configured to independently actuate the first device and wherein the second control mechanism is configured to independently actuate the second device.

5. The apparatus of claim 1 wherein the first lumen and the second lumen converge into the delivery path at the distal section of the catheter body such that only one of the first device or the second device is actuated at a time from the delivery path.

6. The apparatus of claim 1 wherein the first device and the second device is each a needle.

7. The apparatus of claim 1 wherein the first lumen and the second lumen are configured to allow each of the first device and the second device to rotate therein and extend therefrom.

8. The apparatus of claim 7 wherein the first lumen and the second lumen fuse at least at one portion to form the delivery path.

9. The apparatus of claim 8 wherein the delivery path has a cross sectional shape like a numeral Eight (8).

10. An apparatus comprising:
a catheter body having a proximal section, a distal section, and at least a first lumen and a second lumen extending therethrough, the first lumen configured for a first device and the second lumen configured for a second device to be disposed therein, the first lumen and the second lumen being placed side-by-side to one another, wherein there is no separating wall therebetween the first lumen and the second lumen at the distal section of the catheter body; and
a control handle coupled to the catheter body, the control handle including a first control mechanism configured to control a movement of the first device, the first control mechanism including a rotation knob operable to rotate the first device;
a separate second control mechanism configured to control a movement of the second device, the second control mechanism including a rotation knob operable to rotate the second device; and
a first indicator stop operable to limit a distal extension distance movement of the first control mechanism and a separate second indicator stop operable to limit a distal extension distance movement of the second control mechanism,
wherein a delivery path in the distal section of the catheter body is configured such that only one of the first device or the second device is actuated at a time, or is configured such that the delivery path inner dimension is smaller than an outer dimension of the first device and the second device combined, or is configured such that the delivery path is too small to accommodate both the first device and the second device at one time.

11. The apparatus of claim 10 wherein the first lumen and the second lumen form two separate lumens running parallel to one another through the catheter body and fuse to form one delivery path at the distal section of the catheter body, the delivery path has a cross section with 8-like shape.

12. The apparatus of claim 10 wherein the catheter body has a Y-like shape wherein the first lumen and the second lumen are placed into two separate tracks in a proximal section of the catheter body and the first lumen and the second lumen converge into a lumen at the distal section.

13. The apparatus of claim 10 wherein the first control mechanism is configured to independently rotate the first device and wherein the second control mechanism is configured to independently rotate the second device.

14. The apparatus of claim 10 wherein each of the first device and the second device is a needle having a beveled tip and a distal opening at the beveled tip.

15. The apparatus of claim 14 wherein the first device and the second device are positioned to have sides pressed against each other such that beveled tips form one sharp point during an initial delivery state.

* * * * *